United States Patent
Wang et al.

(10) Patent No.: US 6,770,780 B1
(45) Date of Patent: Aug. 3, 2004

(54) VINYLPHENYLPROPIONIC ACID DERIVATIVES, PRODUCTION PROCESS THEREFOR, POLYMER THEREOF AND RADIATION SENSITIVE RESIN COMPOSITION

(75) Inventors: Yong Wang, Tokyo (JP); Yasuaki Mutsuga, Tokyo (JP); Shigeo Shimizu, Tokyo (JP); Tsutomu Shimokawa, Tokyo (JP); Atsushi Kumano, Tokyo (JP)

(73) Assignee: JSR Corporation, Tokyo (JP)

( * ) Notice: Subject to any disclaimer, the term of this patent is extended or adjusted under 35 U.S.C. 154(b) by 100 days.

(21) Appl. No.: 10/129,119
(22) PCT Filed: Nov. 10, 2000
(86) PCT No.: PCT/JP00/07950
§ 371 (c)(1),
(2), (4) Date: May 14, 2002
(87) PCT Pub. No.: WO01/36370
PCT Pub. Date: May 25, 2001

(30) Foreign Application Priority Data

Nov. 15, 1999 (JP) ............................................ 11-324413
May 2, 2000 (JP) ...................................... 2000-133334

(51) Int. Cl.$^7$ ................................................ C07F 9/09
(52) U.S. Cl. ......................................................... 562/8
(58) Field of Search .............................................. 562/8

(56) References Cited

U.S. PATENT DOCUMENTS 5,679,495 A 10/1997 Yamachika et al.

FOREIGN PATENT DOCUMENTS

| JP | 5-61197 | 3/1993 |
| JP | 5-279425 | 10/1993 |
| JP | 7-209868 | 8/1995 |

OTHER PUBLICATIONS

Khan et al., Synlett (Letters), Aug. 1997, pp. 995–997.*
Faiz Ahmed Khan et al., "A Novel Sm(II)–Induced Route to Highly Substituted Benzannulated Cyclooctanol Derivatives", Synlett, Aug. 1997, pp. 995–997, especially, see compound Nos. 2a, 2c, 2, 9.
L. Angiolini et al., "Synthesis and characterization of poly styrenes containing side×chain tributyltin carboxylate moieties like it the aromatic ring through a 1,2–ethylene spacer.", Polymer, 2000, vol. 41, No. 11, pp. 3913–3924, especiallys, see compound No. 5.
T. ishizone, et al., Macromolecules, vol. 32, pp. 1453–1462, "Protection and Polymerization of Functional Monomers, 29. Syntheses of Well–Defined Poly[4–Vinylphenyl)Acetic Acid], Poly[3–(4–Vinylphenyl)Proponic Acid], And Poly (3–Vinylbenzoic Acid) by Means of Anionic Living Polymerizations of Protected Monomers Bearing Bicyclic Ortho Ester Moieties", 1999.
S. Watanabe, et al., Makromol, Chem., vol. 193, pp. 2781–2792, "Emulsion Polymerization of Styrene using Phosphorus with Polymerizable Chain as an Emulsifier", 1992.

* cited by examiner

Primary Examiner—Robert Deshon Harlan
(74) Attorney, Agent, or Firm—Oblon, Spivak, McClelland, Maier & Neustadt, P.C.

(57) ABSTRACT

Vinylphenylpropionic acid derivatives; processes for producing the derivatives; polymers of the same; and radiosensitive resin compositions containing the polymers. The above polymers exhibit low radiation absorption and are useful as the resin component of radiosensitive resin compositions particularly suitable for chemically amplified resists. For example, t-butyl 4-vinylphenylpropionate is produced by (1) reacting t-butyl bromoacetate with tri(n-butyl) phosphine to obtain a quaternary phosphonium salt, (2) reacting this salt with a base to obtain a phosphorus ylide, (3) reacting this ylide with 2,4,6-tris(3',5'-di-t-butyl-4'-hydroxybenzyl)methyl-styrene to obtain a quaternary phosphonium salt, and (4) hydrolyzing this salt.

7 Claims, 10 Drawing Sheets

VINYLPHENYLPROPIONIC ACID DERIVATIVES, PRODUCTION PROCESS THEREFOR, POLYMER THEREOF AND RADIATION SENSITIVE RESIN COMPOSITION

FIELD OF THE INVENTION

The present invention relates to vinylphenylpropionic acid derivatives, a production process therefore, a polymer thereof and a radiation sensitive resin composition. More specifically, it relates to vinylphenylpropionic acid derivatives preferably having an acid decomposable substituent, a production process therefore, a polymer thereof and a radiation sensitive resin composition which comprises the polymer and is useful for lithography using radiation such as far ultraviolet radiation typically from a KrF excimer laser or ArF excimer laser, charged corpuscular beams such as electron beams or X-radiation such as synchrotron radiation.

PRIOR ART

In the field of lithography typically used for the production of integrated circuit elements, the design rule of lithography has been decreasing to obtain higher integration. The development of a lithography process which enables a pattern as fine as 0.5 $\mu$m or less to be formed stably has been under way vigorously. As a result, a lithography process using radiation having a short wavelength (wavelength of 300 nm or less) which is effective in increasing the range of Depth of Focus (DOF) as well as in reducing the design rule has been developed.

Examples of such radiation having a short wavelength include far ultraviolet radiation from a KrF excimer laser (wavelength of 248 nm) or ArF excimer laser (wavelength of 193 nm), X-radiation such as synchrotron radiation and charged corpuscular beams such as electron beams. As a high-resolution resist for use with the above radiation having a short wavelength, International Business Machine (IBM) Corporation has proposed a "chemically amplified resist" and the improvement of this chemically amplified resist is now under way energetically.

The chemically amplified resists are divided into a positive type and a negative type. A positive type chemically amplified resist basically comprises a substance which generates an acid upon exposure to radiation (to be referred to as "radiation sensitive acid generating agent" hereinafter) and a resin which is protected by an acid dissociable group, is insoluble or hardly soluble in an alkali and becomes alkali-soluble when the acid dissociable group is dissociated (to be referred to as "acid dissociable group-containing resin" hereinafter). A resist pattern is formed, making use of a phenomenon that when the resist film is exposed to radiation (to be referred to as "exposure" hereinafter), the radiation sensitive acid generating agent generates an acid, the decomposition reaction of the acid dissociable group is carried out in the resist film by the catalytic function of this acid, and an exposed portion becomes soluble in a developer.

The acid dissociable group-containing resin is obtained by substituting the acidic functional group of a resin containing at least one acidic functional group such as a phenolic hydroxyl group or carboxyl group by at least one acid dissociable group which can be dissociated in the presence of an acid and the resin itself is insoluble or hardly soluble in an alkali. As the acid dissociable group-containing resin having a carboxyl group is generally known a copolymer of acrylic acid or methacrylic acid protected by a t-butyl group or tetrahydropyranyl (THP) group and another monomer. However, a resin containing an acrylic acid or methacrylic acid unit protected by a t-butyl group or THP has low resistance to dry etching and therefore can be used in combination with only a unit having high resistance to dry etching. Then, if there are acid dissociable group-containing monomers having high resistance to dry etching, for example, aliphatic carboxylic acid derivatives having an acid decomposable substituent and substituted by a vinylphenyl group, the resin can be copolymerized with a larger number of monomers, which would be useful for the optimization of a resist resin structure.

Heretofore, the synthesis of a vinylphenylpropionic acid from 4-(2'-chloroethyl)styrene as a starting raw material has been reported (T. Ishizone, et. al, Macromolecules, 1999, 32, 1453-1462, S. Watanabe, et. al, Macromol. Chem. 1992, 193, 2781-2792). However, as this synthesis process is a reaction between a Grignard reagent and carbonic dioxide, it is not suitable for inexpensive and safe industrial-scale production. Further, 4-(2'-chloroethyl)styrene which is a synthesis raw material is not an inexpensive industrial raw material and cannot be easily produced.

As a problem special to this chemically amplified resist, its resist pattern is changed in line width or T-shaped by fluctuations in post-exposure delay (to be referred to as "PED" hereinafter) which is a time from exposure to a heat treatment. In recent years, there have been proposed various chemically amplified resists which can be used for the production of semiconductor devices, including a radiation sensitive resin composition which comprises a polymer consisting of a hydroxystyrene-based recurring unit, a t-butyl (meth)acrylate recurring unit and a recurring unit for reducing the solubility in an alkali developer of the polymer after exposure (JP-A 7-209868) (the term "JP-A" as used herein means an "unexamined published Japanese patent application").

However, along with a recent tendency to reduce the design rule of a semiconductor device, the radiation absorption of a resin which is the main ingredient of a radiation sensitive resin composition used cannot be ignored in a chemically amplified resist in order to increase sensitivity while maintaining the rectangularity of a pattern. It has been difficult to use a conventional chemically amplified resist for the production of a semiconductor device having a fine pattern which is expected to be required from now on.

SUMMARY OF THE INVENTION

In view of the above situation of the prior art, it is an object of the present invention to provide vinylphenylpropionic acid derivatives which may have an acid decomposable substituent.

It is another object of the present invention to provide an industrially advantageous process for producing the vinylphenylpropionic acid derivatives of the present invention.

It is still another object of the present invention to provide a polymer which has extremely low absorption of radiation and is particularly useful as a resin component of a radiation sensitive resin composition suitable for use as a chemically amplified resist.

It is a further object of the present invention to provide a radiation sensitive resin composition which contains the above polymer, can reduce the difference of effective exposure amount between an upper portion and a lower portion of a resist film, can ensure the rectangularity of even a fine pattern, and is useful as a chemically amplified resist having high sensitivity to various types of radiation such as far ultraviolet radiation from an excimer laser, charged corpuscular beams such as electron beams or X-radiation such as synchrotron radiation (small amount of exposure energy).

It is a still further object of the present invention to provide a radiation sensitive resin composition which is free from a change in the line width of a pattern made therefrom and the T-shaped, deformation of the pattern caused by fluctuations in PED and has excellent resolution.

Other objects and advantages of the present invention will become apparent from the following description.

Means for Solving the Problems

According to the present invention, firstly, the above objects and advantages of the present invention are attained by vinylphenylpropionic acid derivatives represented by the following formula (1):

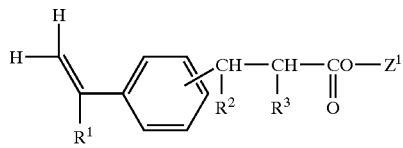
(1)

wherein $R^1$ is a hydrogen atom or a methyl group, $R^2$ and $R^3$ may be the same or different and each a hydrogen atom, an alkyl group having 1 to 8 carbon atoms which may be substituted or a phenyl group which may be substituted, and $Z_1$ is a group represented by the following formula (2):

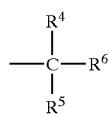
(2)

wherein $R^4$, $R^5$ and $R^6$ may be the same or different and each a hydrogen atom, an alkyl; group having 1 to 8 carbon atoms which may be substituted or a phenyl group which may be substituted, or any two of $R^4$, $R^5$ and $R^6$ may be bonded together with a carbon atom bonded thereto to form a cyclic aliphatic group, or a group represented by the following formula (3):

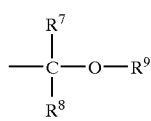
(3)

wherein $R^7$, $R^8$ and $R^9$ may be the same or different and each a hydrogen atom, an alkyl group having 1 to 8 carbon atoms which may be substituted or a phenyl group which may be substituted, or any two of $R^7$, $R^8$ and $R^9$ may be bonded together with a carbon atom bonded thereto to form a cyclic aliphatic group.

Secondly, the above objects and advantages of the present invention are attained by a process for producing vinylphenylpropionic acid derivatives represented by the above formula (1), comprising the steps of:

(i) reacting an acetate represented by the following formula (4-1):

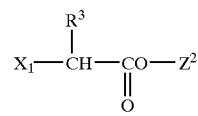
(4-1)

wherein $R^3$ is as defined in the above formula (1), $Z^2$ is a group represented by the following formula (2'):

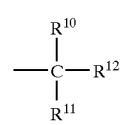
(2')

wherein $R^{10}$, $R^{11}$ and $R^{12}$ may be the same or different and each a hydrogen atom, an alkyl group having 1 to 8 carbon atoms which may be substituted or a phenyl group which may be substituted, or any two of $R^{10}$, $R^{11}$ and $R^{12}$ may be bonded together with a carbon atom bonded thereto to form a cyclic aliphatic group, or a group represented by the above formula (3), and $X_1$ is an eliminating group, with an alkylphosphine represented by the following formula (4-2):

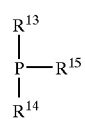
(4-2)

wherein $R^{13}$, $R^{14}$ and $R^{15}$ may be the same or different and each an alkyl group having 1 to 8 carbon atoms which may be substituted, to form a first quaternary phosphonium salt represented by the following formula (4-3):

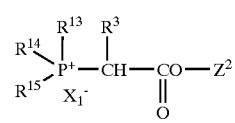
(4-3)

wherein $R^3$ is as defined in the above formula (1), $Z^2$ and $X_1$ are as defined in the above formula (4-1), and $R^{13}$, $R^{14}$ and $R^{15}$ are as defined in the above formula (4-2), (ii) reacting the formed first quaternary phosphonium salt with a base to form a phosphorus ylide represented by the following formula (4-4):

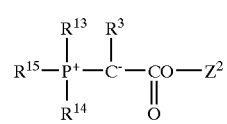
(4-4)

wherein $R^3$ is as defined in the above formula (1), $Z^2$ is as defined in the above formula (4-1), and $R^{13}$, $R^{14}$ and $R^{15}$ are as defined in the above formula (4-2), (iii) reacting the formed phosphorus ylide with a styrene derivative represented by the following formula (4-5):

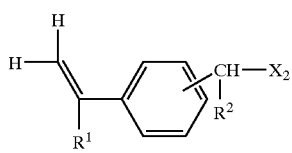

(4-5)

wherein $R^1$ and $R^2$ are as defined in the above formula (1), and $X_2$ is an eliminating group, to form a second quaternary phosphonium salt represented by the following formula (4-6):

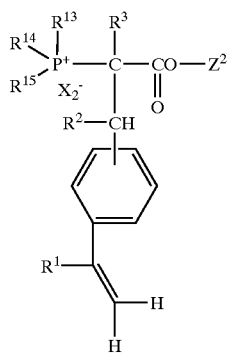

(4-6)

wherein $R^1$, $R^2$ and $R^3$ are as defined in the above formula (1), $Z^2$ is as defined in the above formula (4-1) and $R^{13}$, $R^{14}$ and $R^{15}$ are as defined in the above formula (4-2), and (iv) hydrolyzing the formed quaternary phosphonium salt.

According to the present invention, thirdly, the above objects and advantages of the present invention are attained by a polymer which comprises a recurring unit represented by the following formula (1'):

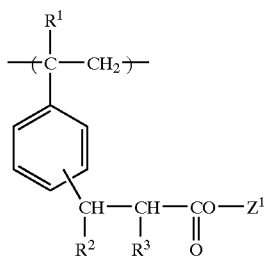

(1')

wherein $R^1$, $R^2$ and $Z^1$ are as defined in the above formula (1), and which as a weight average molecular weight in terms of polystyrene measured by gel permeation chromatography (GPC) of 1,000 to 500,000.

According to the present invention, finally, the above objects and advantages of the present invention are attained by a radiation sensitive resin composition which contains (A) the above polymer of the present invention and (B) a radiation sensitive acid generating agent.

DETAILED DESCRIPTION OF THE PREFERRED EMBODIMENT

Preferable Embodiments of the Invention

Figure 1:
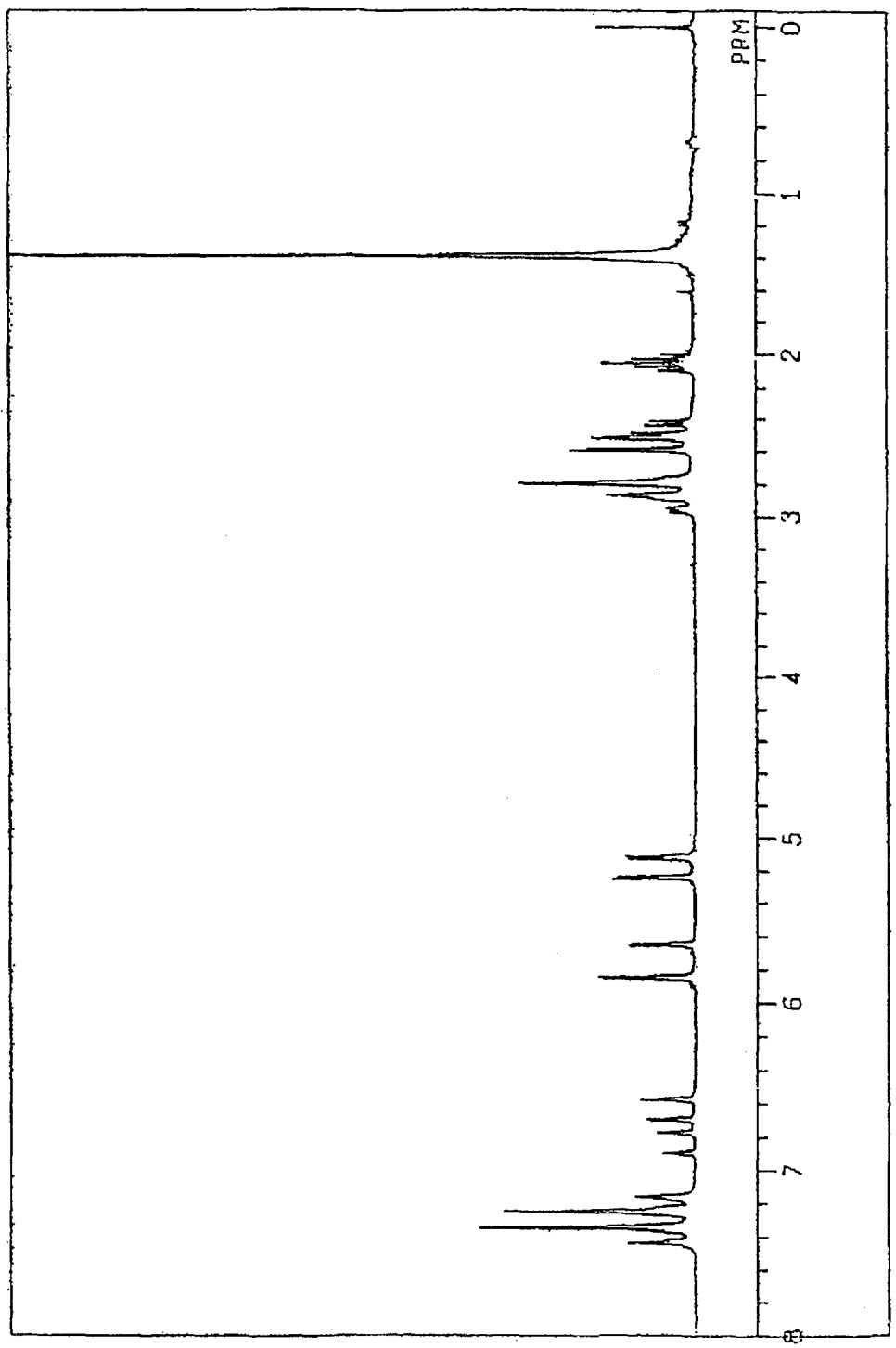
FIG. 1 is a nuclear magnetic resonance spectrum diagram of a compound obtained in Example 1.

The present invention will be described in detail hereinbelow.

Vinylphenylpropionic Acid Derivatives

The vinylphenylpropionic acid derivatives of the present invention is represented by the above formula (1).

In the formula (1), $R^1$ is a hydrogen atom or a methyl group, $R^2$ and $R^3$ may be the same or different and each a hydrogen atom, an alkyl group having 1 to 8 carbon atoms which may be substituted or a phenyl group which may be substituted.

The alkyl group having 1 to 8 carbon atoms which may be substituted may be linear, branched or cyclic. Examples of the alkyl group include methyl group, ethyl group, propyl group, butyl group, hexyl group, cyclohexyl group, octyl group and decyl group. The substituent is an alkoxyl group such as methoxyl group or ethoxyl group; or halogen atom such as fluorine, chlorine, bromine or iodine.

The substituent of the phenyl group which may be substituted is an alkyl group such as methyl group, ethyl group, n-propyl group or i-propyl group; alkoxyl group such as methoxyl group or ethoxyl group; or halogen atom such as fluorine, chlorine, bromine or iodine.

In the formula (1), $Z^1$ is a group represented by the above formula (2) or (3). $R^4$, $R^5$ and $R^6$ in the formula (2) may be the same or different and each a hydrogen atom, an alkyl group having 1 to 8 carbon atoms which may be substituted or a phenyl group which may be substituted, or any two of $R^4$, $R^5$ and $R^6$ may be bonded together with a carbon atom bonded thereto to form a cyclic aliphatic group.

In the formula (1), the bonding position of —$CHR^2CHR^3COOZ^1$ is not particularly limited but preferably the para-position from the viewpoints of acquisition ease of a raw material and performance when the obtained product is used as a resist material.

In the formula (3), $R^7$ and $R^8$ may be the same or different and each a hydrogen atom, an alkyl group having 1 to 8 carbon atoms which may be substituted or a phenyl group which may be substituted, and $R^9$ is an alkyl group having 1 to 8 carbon atoms which may be substituted or a phenyl group which may be substituted, or any two of $R^7$, $R^8$ and $R^9$ may be bonded together with a carbon atom bonded thereto to form a cyclic aliphatic group.

Examples of the alkyl group having 1 to 8 carbon atoms which may be substituted and the phenyl group which may be substituted in the formulas (2) and (3) are the same as those listed for the formula (1).

The above cyclic aliphatic group in the formulas (2) and (3) is preferably a 5- to 7-membered ring, particularly preferably a 6-membered ring, for example, a cyclohexylidene group in the formula (2) and 2-oxacyclclopentylidene or 2-oxacyclohexylidene group in the formula (3).

In the above formula (1), the group represented by

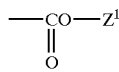

is preferably an acid dissociable group which generates a carboxyl group (—COOH) in the presence of an acid. Examples of the acid dissociable group include linear, branched and cyclic alkoxycarbonyl groups such as methoxycarbonyl group, ethoxycarbonyl group, n-propoxycarbonyl group, i-propoxycarbonyl group, n-butoxycarbonyl group, 2-methylpropoxycarbonyl group, 1-methylpropoxycarbonyl group, t-butoxycarbonyl group, n-pentyloxycarbonyl group, t-pentyloxycarbonyl group, n-hexyloxycarbonyl group, 1-methyl-1-ethylpropoxycarbonyl group, n-heptyloxycarbonyl group, 1,1-dimethylpentyloxycarbonyl group, 1,1-dimethyl-3-methylbutoxycarbonyl group, n-octyloxycarbonyl group, n-nonyloxycarbonyl group, n-decyloxycarbonyl group, cyclopentyloxycarbonyl group, cyclohexyloxycarbonyl group, 1-methylcyclohexyloxycarbonyl group, 4-t-butylcyclohexyloxycarbonyl group, cycloheptyloxycarbonyl group, cyclooctyloxycarbonyl group and 1-methyl-1-cyclohexylpropoxycarbonyl group: aryloxycarbonyl groups such as phenoxycarbonyl group, 4-t-butylphenoxycarbonyl group and 1-naphthyloxycarbonyl group; aralkyloxycarbonyl groups such as benzyloxycarbonyl group, 4-t-butylbenzyloxycarbonyl group, phenetyloxycarbonyl group, 4-t-butylphenetyloxycarbonyl group, 1-methyl-1-phenylethoxycarbonyl group and 1-phenyl-1-(4'-methylphenyl)ethoxycarbonyl group; linear, branched and cyclic 1-alkpxyethoxycarbonyl groups such as 1-methoxyethoxycarbonyl group, 1-ethoxyethoxycarbonyl group, 1-n-propoxyethoxycarbonyl group, 1-i-propoxyethoxycarbonyl group, 1-n-butoxyethoxycarbonyl group, 1-(2'-methylpropoxy)ethoxycarbonyl group, 1-(1'-methylpropoxy)ethoxycarbonyl group, 1-t-butoxyethoxycarbonyl group, 1-cyclohexyloxyethoxycarbonyl group and 1-(4'-t-butylcyclohexyloxy)ethoxycarbonyl group; 1-aryloxyethoxycarbonyl groups such as 1-phenoxyethoxycarbonyl group, 1-(4'-t-butylphenoxy)ethoxycarbonyl group and 1-(1'-naphthyloxy)ethoxycarbonyl group; 1-aralkyloxyethoxycarbonyl groups such as 1-benzyloxyethoxycarbonyl group, 1-(4'-t-butylbenzyloxy)ethoxycarbonyl group, 1-phenetyloxyethoxycarbonyl group and 1-(4'-t-butylphenetyloxy)ethoxycarbonyl group; linear, branched and cyclic alkoxycarbonylmethoxycarbonyl groups such as methoxycarbonylmethoxycarbonyl group, ethoxycarbonylmethoxycarbonyl group, n-propoxycarbonylmethoxycarbonyl group, i-propoxycarbonylmethoxycarbonyl group, n-butoxycarbonylmethoxycarbonyl group, 2-methylpropoxycarbonylmethoxycarbonyl group, 1-methylpropoxycarbonylmethoxycarbonnyl group, t-butoxycarbonylmethoxycarbonyl group, cyclohexyloxycarbonylmethoxycarbonyl group and 4-t-butylcyclohexyloxycarbonylmethoxycarbonyl group; linear, branched and cyclic alkoxycarbonylmethyl groups such as methoxycarbonylmethyl group, ethoxycarbonylmethyl group, n-propoxycarbonylmethyl group, i-propoxycarbonylmethyl group, n-butoxycarbonylmethyl group, 2-methylpropoxycarbonylmethyl group, 1-methylpropoxycarbonylmethyl group, t-butoxycarbonylmethyl group, cyclohexyloxycarbonylmethyl group and 4-t-butylcyclohexyloxycarbonylmethyl group; aryloxycarbonylmethyl groups such as phenoxycarbonylmethyl group, 4-t-butylphenoxycarbonylmethyl group and 1-naphthyloxycarbonylmethyl group; aralkyloxycarbonylmethyl groups such as benzyloxycarbonylmethyl group, 4-t-butylbenzyloxycarbonylmethy group, phenetyloxycarbonylmethyl group and 4-t-butylphenetyloxycarbonylmethyl group; linear, branched and cyclic 2-alkoxycarbonylethyl groups such as 2-methoxycarbonylethyl group, 2-ethoxycarbonylethyl group, 2-n-propoxycarbonylethyl group, 2-i-propoxycarbonylethyl group, 2-n-butoxycarbonylethyl group, 2-(2'-methylpropoxy)carbonylethyl group, 2-(1'-methylpropoxy)carbonylethyl group, 2-t-butoxycarbonylethyl group, 2-cyclohexyloxycarbonylethyl group and 2-(4'-t-butylcyclohexyloxycarbonyl)ethyl group; 2-aryloxycarbonylethyl groups such as 2-phenoxycarbonylethyl group, 2-(4'-t-butylphenoxycarbonyl)ethyl group and 2-(1'-naphthyloxycarbonyl)ethyl group; 2-aralkyloxycarbonylethyl groups such as 2-benzyloxycarbonylethyl group, 2-(4'-t-butylbenzyloxycarbonyl)ethyl group, 2-phenetyloxycarbonylethyl group and 2-(4'-t-butylphenetyloxycarbonyl)ethyl group; and 1-methyl-i-n-butoxypropoxycarbonyl group, 1-phenylcyclohexyloxycarbonyl group, (cyclohexyl)(phenoxy)methoxycarbonyl group, 1-phenyl-1-cyclohexyloxyethoxycarbonyl group, (cyclohexyl)(phenyl)(methoxy)methoxycarbonyl group, 2-tetrahydrofuranyloxycarbonyl group, 2-(2-methyltetrahydrofuranyl)oxycarbonyl group, 2-tetrahydropyranyloxycarbonyl group, 2-(2,5-dimethyltetrahydropyranyl)oxycarbonyl group and 2-(2-phenyltetrahydropyranyl)oxycarbonyl group.

Examples of the compound represented by the above formula (1) include compounds represented by the following formulas (6-1) to (6-32) (compounds of the formula (1) in which $Z^1$ is a group of the formula (2)) and compounds represented by the following formulas (7-1) to (7-22) (compounds of the formula (1) in which $Z^1$ is a group of the formula (3)). Out of these, compounds in which the bonding position is the para-position are preferred.

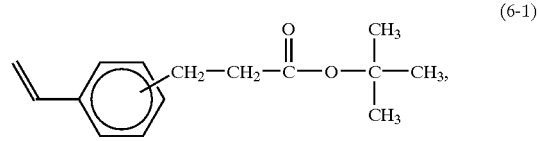

(6-1)

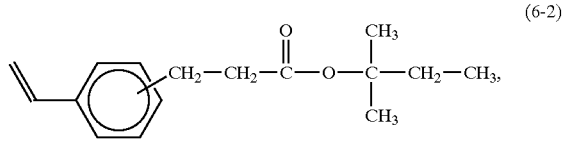

(6-2)

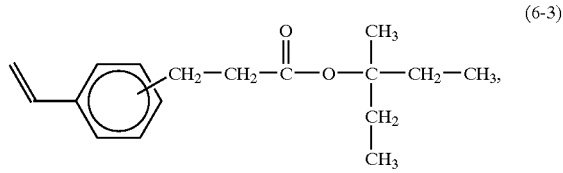

(6-3)

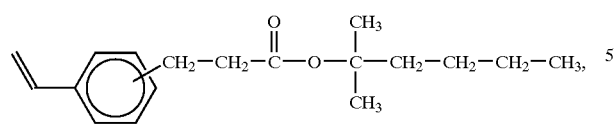
(6-4)
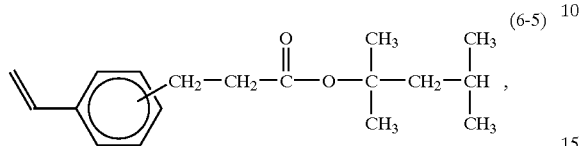
(6-5)
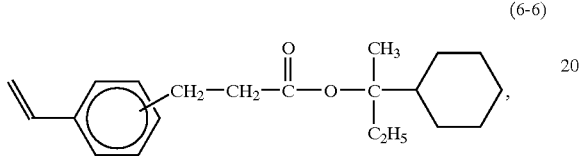
(6-6)
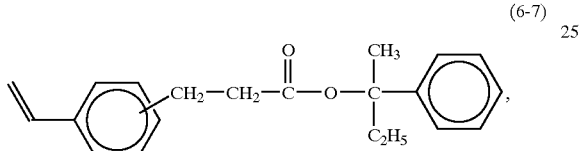
(6-7)
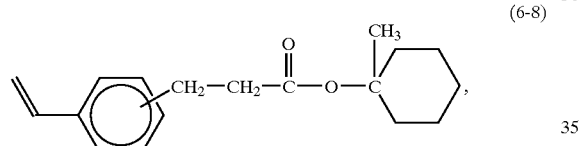
(6-8)
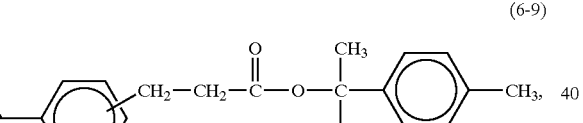
(6-9)
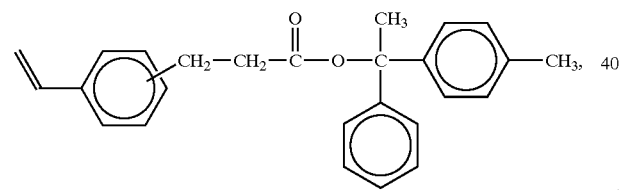
(6-10)
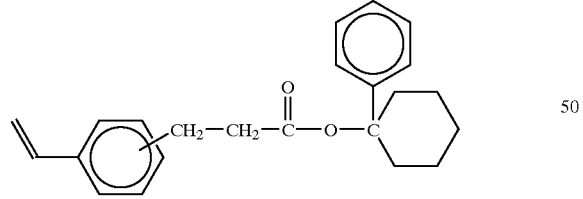
(6-11)
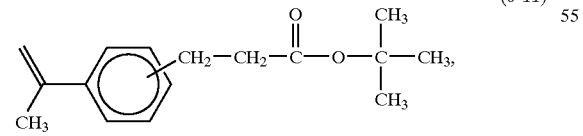
(6-12)
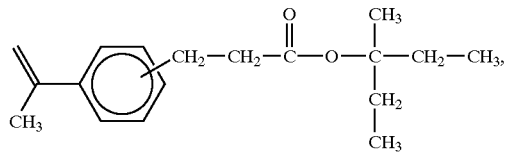
(6-13)
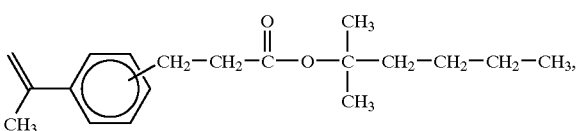
(6-14)
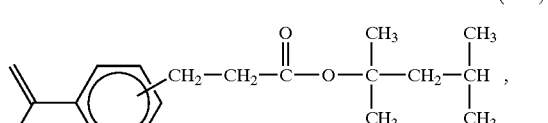
(6-15)
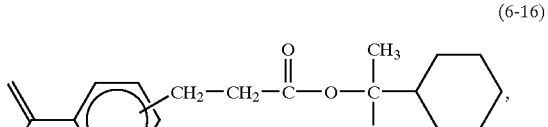
(6-16)
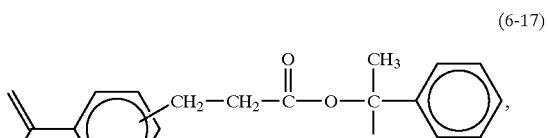
(6-17)
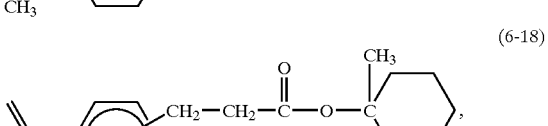
(6-18)
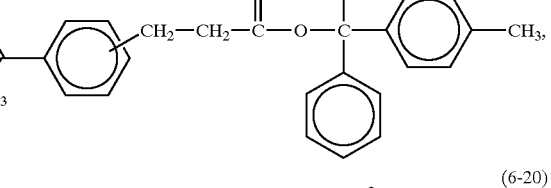
(6-19)
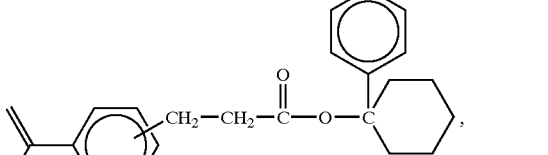
(6-20)
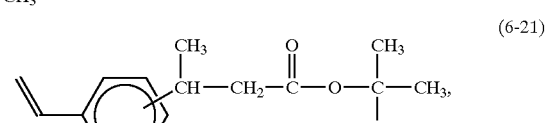
(6-21)

-continued
(6-22) 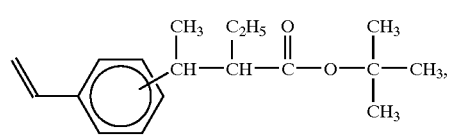
(6-23) 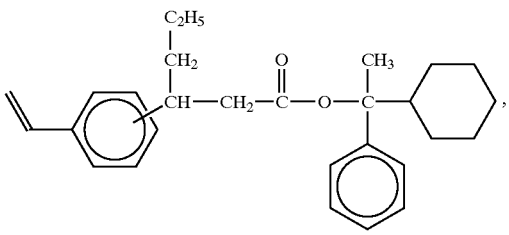
(6-24) 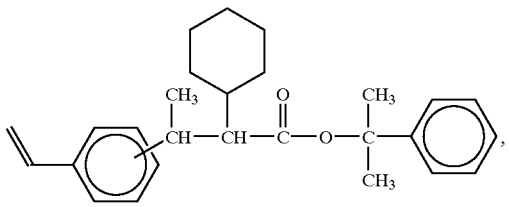
(6-25) 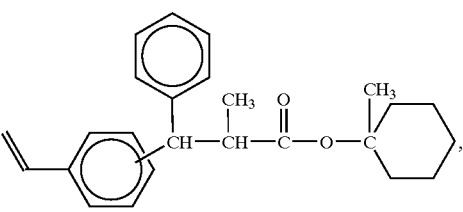
(6-26) 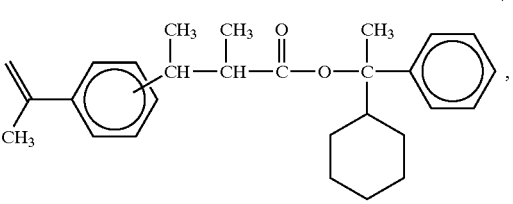
(6-27) 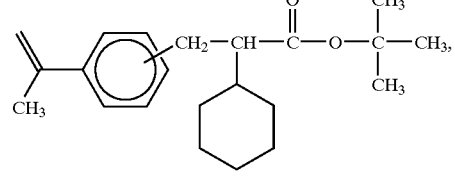
(6-28) 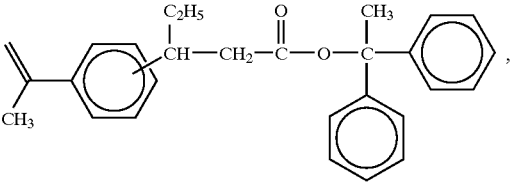
-continued
(6-29) 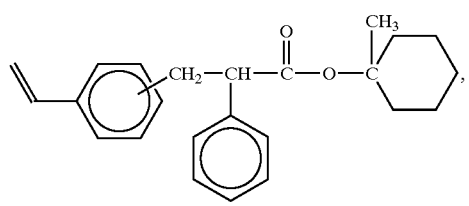
(6-30) 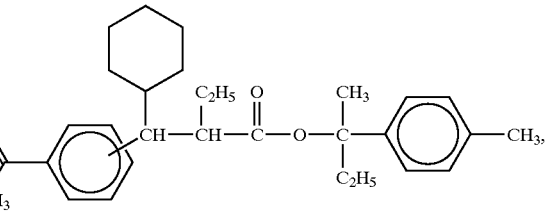
(6-31) 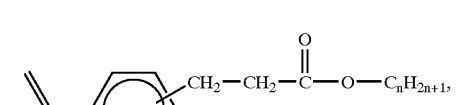
(6-32) 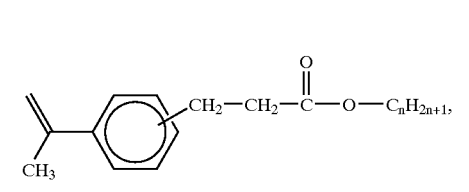
(n is an integer of 1 to 30)
(7-1) 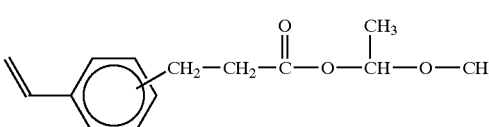
(7-2) 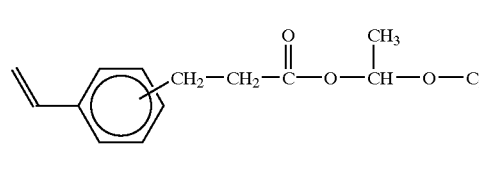
(7-3) 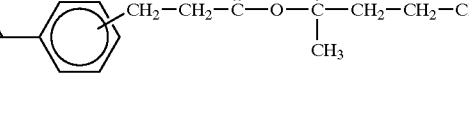
(7-4) 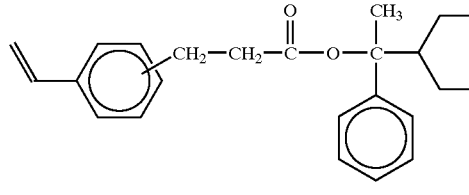

-continued (7-5) 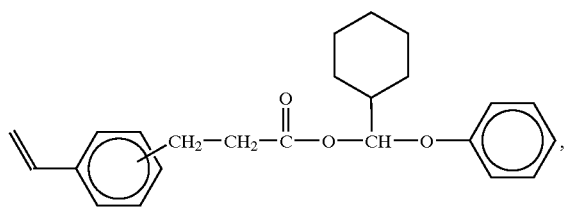

(7-6) 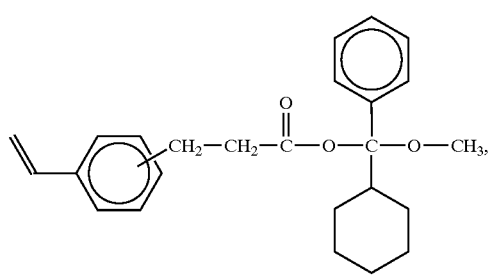

(7-7) 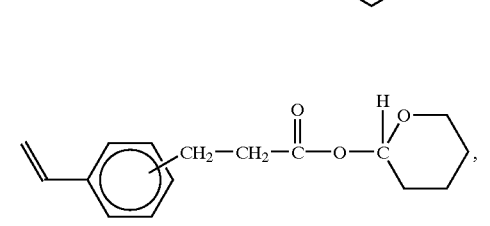

(7-8) 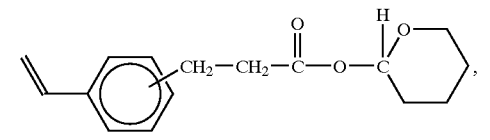

(7-9) 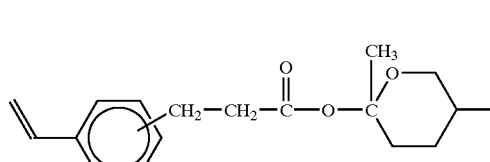

(7-10) 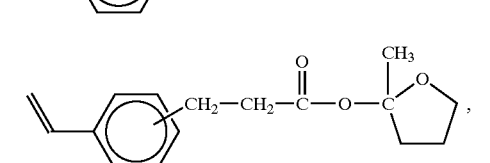

(7-11) 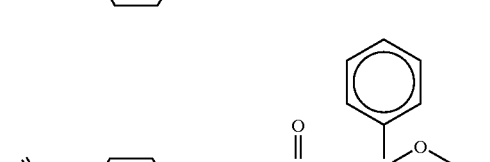

(7-12) 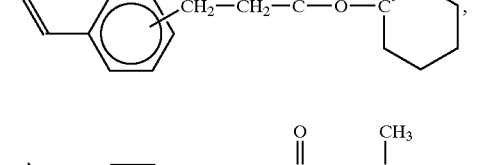

-continued (7-13) 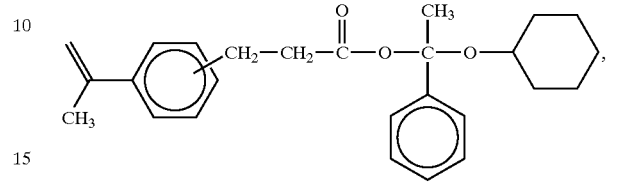

(7-14) 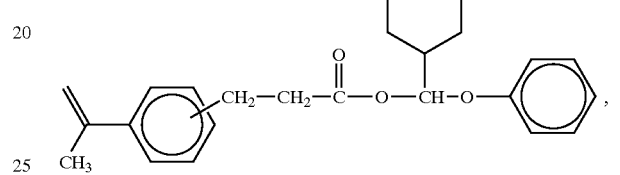

(7-15) 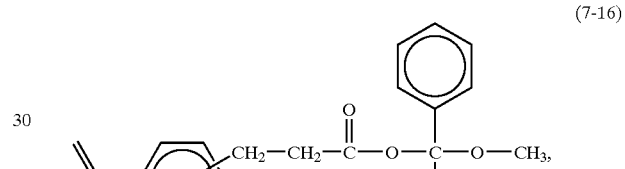

(7-16) 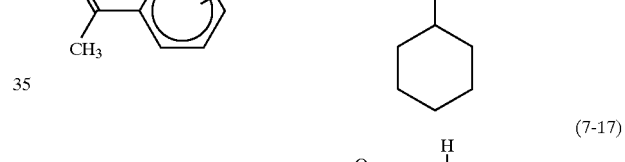

(7-17) 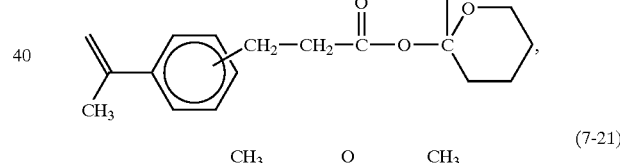

(7-21) 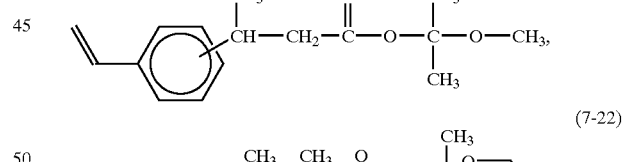

(7-22) 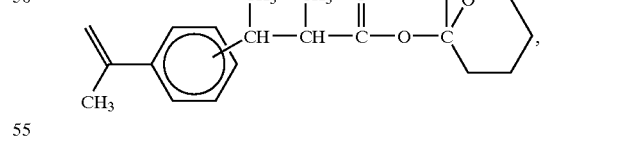

Since these vinylphenylpropionic acid derivatives have an acid decomposable group in the side chain, polymers obtained by homopolymerizing the derivatives alone or copolymerizing them with other monomers can be changed in polarity because a hydrophobic alkoxycarbonyl group is decomposed by an acid to become an oxycarbonyl group having high hydrophilic nature. Since these vinylphenylpropionic acid derivatives have a benzene ring having high resistance to dry etching, they can be combined with various monomers for the design of a resist resin, which is useful for the optimization of a resist: resin structure.

Production of Vinylphenylpropionic Acid Derivatives

The vinylphenylpropionic acid derivatives of the present invention can be advantageously produced by the process of the present invention which comprises the steps (i) to (iv) as described above.

In the step (i), an ethyl acetate represented by the formula (4-1) and a trialkylphosphine represented by the formula (4-2) are reacted with each other.

In the formula (4-1), $R^3$ is as defined in the formula (1) and its examples are the same as those listed above. In the formula (4-1), $Z^2$ is a group represented by the above formula (2') or (3). $R^{10}$, $R^{11}$ and $R^{12}$ in the formula (2') are the same as $R^4$, $R^5$ and $R^6$ in the formula (2). In the formula (4-1), $X_1$ is an eliminating group and its examples are those which are generally used for organic synthesis, for example, halogen atoms such as chlorine, bromine and iodine, and sulfonyl groups such as methylsulfonyl group and p-methylphenylsulfonyl group.

The trialkylphosphine used in the step (i) is not particularly limited but preferably triethylphosphine, tri-n-butylphosphine or tricyclohexylphosphine.

The reaction in the step (i) is preferably carried out at −10 to +80° C. for 2 to 40 hours. The reaction temperature and time are more preferably +10 to +50° C. and 4 to 10 hours, respectively. The reaction is preferably carried out in a nitrogen atmosphere. The solvent used in the reaction of the step (i) is preferably a water-miscible nonprotonic organic solvent. Examples of the solvent include tetrahydrofuran, 1,4-dioxane, N,N-dimethylformamide, dimethyl sulfoxide and acetonitrile. The first quaternary phosphonium salt represented by the above formula (4-3) is formed by the reaction of the step (i). The definitions and illustrative examples of $R^3$, $Z^2$ and $X_1$ in the formula (4-3) are as described above.

In the step (ii), the first quaternary phosphonium salt formed in the step (i) and a base are reacted with each other.

As the base may be used various bases having strong basicity or super strong basicity. Illustrative examples of the base include 1,5-diazabicyclo[4.3.0]nonene-5,1,8-diazabicyclo[5.4.0]undecene-7, potassium (sodium or lithium) methoxide, potassium (sodium or lithium) ethoxide, potassium (sodium or lithium) n-propoxide, potassium (sodium or lithium) isopropoxide, potassium (sodium or lithium) n-butoxide, potassium (sodium or lithium) sec-butoxide, potassium (sodium or lithium) isobutoxide, potassium (sodium or lithium) t-butoxide, lithium diisopropylamide, lithium (sodium, potassium or calcium) hydride, methyl lithium and n-butyl (sec-butyl or t-butyl) lithium. The reaction in the step (ii) is preferably carried out at −80 to +80° C. It is desirably carried out at +20 to +50° C. in the case of a strong base and −20° C. or less in the case of a super strong base. The reaction time is preferably 0.25 to 10 hours, more preferably 0.5 to 2 hours.

The phosphorus ylide represented by the above formula (4-4) is formed by the reaction in the step (ii). In the formula (4-4), the definitions and examples of $R^3$ and $Z^2$ are as described above.

In the step (iii), the phosphorus ylide formed in the step (ii) is reacted with a styrene derivative represented by the formula (4-5).

In the formula (4-5), the definitions and examples of $R^1$ and $R^2$ are as described above. $X_2$ is an eliminating group and its examples are the same as those listed for $X_1$ in the formula (4-1). The temperature and the reaction time in the step (iii) are preferably 0 to +80° C. and 1 to 96 hours, more preferably +20 to +50° C. and 2 to 48 hours, respectively.

The second quaternary phosphonium salt represented by the formula (4-6) is formed by the reaction in the step (iii). The definitions and examples of $R^1$, $R^2$, $R^3$ and $Z^2$ in the formula (4-6) are as described above.

Finally, the second quaternary phosphonium salt formed in the step (iii) is hydrolyzed in the step (iv).

The reaction temperature and the reaction time in the step (iv) are preferably 0 to +80° C. and 1 to 48 hours, more preferably +20 to +50° C. and 2 to 24 hours, respectively. The alkali aqueous solution used in this reaction may be an aqueous solution of an ordinary inorganic or organic base. Examples of the base include sodium (or potassium) bicarbonate, sodium (or potassium), sodium (or potassium) carbonate, sodium (or potassium) hydroxide, ammonia, tetramethylammonium carbonate (or hydroxide), tetrabutylammonium carbonate (or hydroxide), triethylamine and 1,5-diazabicyclo[4.3.0]nonene-5,1,8-dizabicyclo [5.4.0] undecene-7.

The reaction solvent used for the hydrolytic reaction in the step (iv) is water or a mixed solvent of water and an organic solvent. When the mixed solvent is used, an organic solvent miscible with water, for example, methanol, ethanol, tetrahydrofuran, 1,4-dioxane, N,N-dimethylformamide, dimethyl sulfoxide or acetonitrile is particularly preferred.

The reaction temperature and the reaction time in the step (iv) are 0 to +100° C. and 0.25 to 96 hours, more preferably +20 to +80° C. and 1 to 24 hours, respectively.

The production process comprising the above steps (i) to (iv) can be carried out in one pot. The reaction solvents used in the step (ii) and the step (iii) may be the same organic solvent as the reaction solvent used in the step (i) or a mixed solvent containing the reaction solvent used in the step (i).

Alternatively, the vinylphenylpropionic acid derivatives of the present invention may be produced by hydrolyzing methyl (or ethyl) vinylphenylpropionate represented by the following formula (5-1):

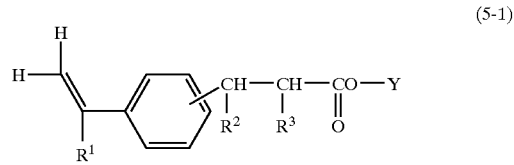

(5-1)

wherein $R^1$, $R^2$ and $R^3$ are as defined in the above formula (1), and Y is a methyl group or an ethyl group, to form a vinylphenylpropionic acid represented by the following formula (5-2):

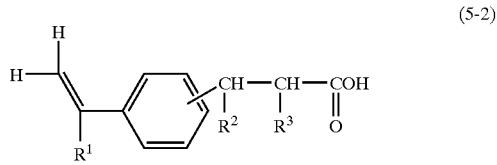

(5-2)

wherein $R^1$, R2 and $R^3$ are as defined in the above formula (1), and esterifying this vinylphenylpropionic acid with a corresponding esterifying agent such as an alcohol. This process is particularly useful when the chemical stability of the carboxylic acid derivative represented by the above formula (4-1) is poor.

The above hydrolytic reaction can be carried out by a generally known method for hydrolyzing a carboxylate. The esterification reaction can be carried out by a general method for esterifying a carboxylate or an addition reaction between a carboxylic acid and an olefin.

In all the reactions in the above production process of the present invention and the alternative process, a polymerization inhibitor is desirably used to prevent a polymerization reaction. Examples of the polymerization inhibitor include commercially available polymerization inhibitors such as 2,6-di-t-butylphenol, 2,6-di-t-butyl-4-ethylphenol and 2,4,6-tris(3',5'-di-t-butyl-4'-hydroxybenzyl)mesitylene. The amount of the polymerization inhibitor is preferably 0.001 to 20 wt %, more preferably 1.1 to 10 wt % based on the total of all the raw materials used in the reactions except the solvent.

Polymer

The polymer in the present invention is a polymer (to be referred to as "polymer (A)" hereinafter) which comprises a recurring unit (to be referred to as "recurring unit (1')" hereinafter) represented by the above formula (1') as an essential unit.

The content of the recurring unit (1') in the polymer (A) is preferably 5 to 80 wt %.

The monomer which provides the recurring unit (1') is a vinylphenylpropionic acid derivative represented by the above formula (1).

The polymer (A) can have a unit derived from a monofunctional monomer (to be referred to as "other recurring unit (α)" hereinafter) having one polymerizable unsaturated bond and/or a unit (to be referred to as "other recurring unit (β)" hereinafter) derived from a polyfunctional monomer having two or more polymerizable unsaturated bonds in addition to the recurring unit (1').

Monomers which provide the other recurring unit (α) include styrene-based monomers which may be substituted by a linear, branched or cyclic alkyl group, such as styrene, α-methylstyrene, o-methylstyrene, m-methylstyrene and p-methylstyrene; styrene-based monomers substituted by a hydroxyl group, such as o-hydroxystyrene, m-hydroxystyrene, p-hydroxystyrene and p-hydroxy-α-methylstyrene; styrene-based monomers substituted by a linear, branched or cyclic alkoxyl group, such as o-methoxystyrene, m-methoxystyrene, p-methoxystyrene, o-t-butoxystyrene, m-t-butoxystyrene, p-t-butoxystyrene and p-cyclohexyloxystyrene; styrene-based monomers substituted by a linear, branched or cyclic 1-alkoxyethoxy group and styrene-based monomers substituted by a 1-aralkyloxyethoxy group, such as p-(1-methoxyethoxy)styrene, p-(1-ethoxyethoxy)styrene, p-(1-n-propoxyethoxy)styrene, p-(1-i-propoxyethoxy)styrene, p-(1-n-butoxyethoxy)styrene, p-(1-t-butoxyethoxy)styrene, p-(1-n-pentyloxyethoxy)styrene, p-(1-n-hexyloxyethoxy)styrene, p-(1-cyclopentyloxyethoxy)styrene, p-(1-cyclohexyloxyethoxy)styrene, p-(1-benzyloxyethoxy)styrene and p-{1-(1'-naphthylmethoxy)ethoxy}styrene; styrene-based monomers substituted by a linear, branched or cyclic 1-alkoxypropoxy group and styrene-based monomers substituted by a 1-aralkyloxypropoxy group, such as p-(1-methoxypropoxy)styrene, p-(1-ethoxypropoxy)styrene, p-(1-n-propoxypropoxy)styrene, p-(1-i-propoxypropoxy)styrene, p-(1-n-butoxypropoxy)styrene, p-(1-t-butoxypropoxy)styrene, p-(1-n-pentyloxypropoxy)styrene, p-(1-n-hexyloxypropoxy)styrene, p-(1-cyclopentyloxypropoxy)styrene, p-(1-cyclohexyloxypropoxy)styrene, p-(1-benzyloxypropoxy)styrene and p-{1-(1'-naphthylmethoxy)propoxy}styrene; styrene-based monomers substituted by a linear, branched or cyclic 1-alkoxy-1-methylethoxy group and styrene-based monomers substituted by a 1-aralkyloxy-1-methylethoxy group, such as p-(1-methoxy-1-methylethoxy)styrene, p-(1-ethoxy-1-methylethoxy)styrene, p-(1-n-propoxy-1-methylethoxy)styrene, p-(1-i-propoxy-1-methylethoxy)styrene, p-(1-n-butoxy-1-methylethoxy)styrene, p-(1-t-butoxy-1-methylethoxy)styrene, p-(1-n-pentyloxy-1-methylethoxy)styrene, p-(1-n-hexyloxy-1-methylethoxy)styrene, p-(1-cyclopentyloxy-1-methylethoxy)styrene, p-(1-cyclohexyloxy-1-methylethoxy)styrene, p-(1-benzyloxy-1-methylethoxy)styrene and p-{1-(1'-naphthylmethoxy)-1-methylethoxy}styrene; styrene-based monomers substituted by a linear, branched or cyclic 1-alkoxybutoxy group and styrene-based monomers substituted by a 1-aralkyloxybutoxy group, such as p-(1-methoxybutoxy)styrene, p-(1-ethoxybutoxy)styrene, p-(1-n-propoxybutoxy)styrene, p-(1-i-propoxybutoxy)styrene, p-(1-n-butoxybutoxy)styrene, p-(1-t-butoxybutoxy)styrene, p-(1-n-pentyloxybutoxy)styrene, p-(1-n-hexyloxybutoxy)styrene, p-(1-cyclopentyloxybutoxy)styrene, p-(1-cyclohexyloxybutoxy)styrene, p-(1-benzyloxybutoxy)styrene and p-{1-(1'-naphthylmethoxy)butoxy}styrene; styrene-based monomers substituted by a linear, branched or cyclic 1-alkoxy-2-methylpropoxy group and styrene-based monomers substituted by a 1-aralkyloxy-2-methylpropoxy group, such as p-(1-methoxy-2-methylpropoxy)styrene, p-(1-ethoxy-2-methylpropoxy)styrene, p-(1-n-propoxy-2-methylpropoxy)styrene, p-(1-i-propoxy-2-methylpropoxy)styrene, p-(1-n-butoxy-2-methylpropoxy)styrene, p-(1-t-butoxy-2-methylpropoxy)styrene, p-(1-n-pentyloxy-2-methylpropoxy)styrene, p-(1-n-hexyloxy-2-methylpropoxy)styrene, p-(1-cyclopentyloxy-2-methylpropoxy)styrene, p-(1-cyclohexyloxy-2-methylpropoxy)styrene, p-(1-benzyloxy-2-methylpropoxy)styrene and p-{1-(1'-naphthylmethoxy)-2-methylpropoxy}styrene; styrene-based monomers substituted by a linear, branched or cyclic 1-alkoxy-1-methylpropoxy group and styrene-based monomers substituted by a 1-aralkyloxy-1-methylpropoxy group, such as p-(1-methoxy-1-methylpropoxy)styrene, p-(1-ethoxy-1-methylpropoxy)styrene, p-(1-n-propoxy-1-methylpropoxy)styrene, p-(1-i-propoxy-1-methylpropoxy)styrene, p-(1-n-butoxy-1-methylpropoxy)styrene, p-(1-t-butoxy-1-methylpropoxy)styrene, p-(1-n-pentyloxy-1-methylpropoxy)styrene, p-(1-n-hexyloxy-1-methylpropoxy)styrene, p-(1-cyclopentyloxy-1-methylpropoxy)styrene, p-(1-cyclohexyloxy-1-methylpropoxy)styrene, p-(1-benzyloxy-1-methylpropoxy)styrene and p-{1-(1'-naphthylmethoxy)-1-methylpropoxy}styrene; styrene-based monomers substituted by a linear, branched or cyclic 1-alkoxypentyloxy group and styrene-based monomers substituted by a 1-aralkyloxypentyloxy group, such as p-(1-methoxypentyloxy)styrene, p-(1-ethoxypentyloxy)styrene, p-(1-n-propoxypentyloxy)styrene, p-(1-i-propoxypentyloxy)styrene, p-(1-n-butoxypentyloxy)styrene, p-(1-t-butoxypentyloxy)styrene, p-(1-n-pentyloxypentyloxy)styrene, p-(1-n-hexyloxypentyloxy)styrene, p-(1-cyclopentyloxypentyloxy)styrene, p-(1-cyclohexyloxypentyloxy)styrene, p-(1-benzyloxypentyloxy)styrene and p-{1-(1'-naphthylmethoxy)pentyloxy}styrene; styrene-based monomers substituted by a linear, branched or cyclic 1-alkoxy-1-methylbutoxy group and styrene-monomers substituted by a 1-aralkyloxy-1-methylbutoxy group, such as p-(1-methoxy-1-methylbutoxy)styrene, p-(1-ethoxy-1- methylbutoxy)styrene, p-(1-n-propoxy-1-methylbutoxy) styrene, p-(1-i-propoxy-1-methylbutoxy)styrene, p-(1-n-butoxy-1-methylbutoxy)styrene, p-(1-t-butoxy-1-methylbutoxy)styrene, p-(1-n-pentyloxy-1-methylbutoxy) styrene, p-(1-n-hexyloxy-1-methylbutoxy)styrene, p-(1-cyclopentyloxy-1-methylbutoxy)styrene, p-(1-cyclohexyloxy-1-methylbutoxy)styrene, p-(1-benzyloxy-1-methylbutoxy)styrene and p-{1-(1'-naphthylmethoxy)-1-methylbutoxy}styrene; styrene-based monomers substituted by a linear, branched or cyclic 1-alkoxy-1,2-dimethylpropoxy group and styrene-based monomers substituted by a 1-aralkyloxy-1,2-dimethylpropoxy group, such as p-(1-methoxy-1,2-dimethylpropoxy)styrene, p-(1-ethoxy-1,2-dimethylpropoxy)styrene, p-(1-n-propoxy-1,2-dimethylpropoxy)styrene, p-(1-i-propoxy-1,2-dimethylpropoxy)styrene, p-(1-n-butoxy-1,2-dimethylpropoxy)styrene, p-(1-t-butoxy-1,2-dimethylpropoxy)styrene, p-(1-n-pentyloxy-1,2-dimethylpropoxy)styrene, p-(1-n-hexyloxy-1,2-dimethylpropoxy)styrene, p-(1-cyclopentyloxy-1,2-dimethylpropoxy)styrene, p-(1-cyclohexyloxy-1,2-dimethylpropoxy)styrene, p-(1-benzyloxy-1,2-dimethylpropoxy)styrene and p-{1-(1'-naphthylmethoxy)-1,2-dimethylpropoxy}styrene; styrene-based monomers substituted by a linear, branched or cyclic 1-alkoxy-2,2-dimethylpropoxy group and styrene-based monomers substituted by a 1-aralkyloxy-2,2-dimethylpropoxy group, such as p-(1-methoxy-2,2-dimethylpropoxy)styrene, p-(1-ethoxy-2,2-dimethylpropoxy)styrene, p-(1-n-propoxy-2,2-dimethylpropoxy)styrene, p-(1-i-propoxy-2,2-dimethylpropoxy)styrene, p-(1-n-butoxy-2,2-dimethylpropoxy)styrene, p-(1-t-butoxy-2,2-dimethylpropoxy)styrene, p-(1-n-pentyloxy-2,2-dimethylpropoxy)styrene, p-(1-n-hexyloxy-2,2-dimethylpropoxy)styrene, p-(1-cyclopentyloxy-2,2-dimethylpropoxy)styrene, p-(1-cyclohexyloxy-2,2-dimethylpropoxy)styrene, p-(1-benzyloxy-2,2-dimethylpropoxy)styrene and p-{1-(1'-naphthylmethoxy)-2,2-dimethylpropoxy}styrene; styrene-based monomers substituted by a linear, branched or cyclic l-alkoxy-1-methylpentyloxy group and styrene-based monomers substituted by a 1-aralkyloxy-1-methylpentyloxy group, such as p-(1-methoxy-1-methylpentyloxy)styrene, p-(1-ethoxy-1-methylpentyloxy)styrene, p-(1-n-propoxy-1-methylpentyloxy)styrene, p-(1-i-propoxy-1-methylpentyloxy)styrene, p-(1-n-butoxy-1-methylpentyloxy)styrene, p-(1-t-butoxy-1-methylpentyloxy)styrene, p-(1-n-pentyloxy-1-methylpentyloxy)styrene, p-(1-n-hexyloxy-1-methylpentyloxy)styrene, p-(1-cyclopentyloxy-1-methylpentyloxy)styrene, p-(1-cyclohexyloxy-1-methylpentyloxy)styrene, p-(1-benzyloxy-1-methylpentyloxy)styrene and p-{l-(1'-naphthylmethoxy)-1-methylpentyloxy}styrene; styrene-based monomers substituted by a linear, branched or cyclic l-alkoxy-1,2,2-trimethylpropoxy group and styrene-based monomers substituted by a 1-aralkyloxy-1,2,2-trimethylpropoxy group, such as p-(1-methoxy-1,2,2-trimethylpropoxy)styrene, p-(1-ethoxy-1,2,2-trimethylpropoxy)styrene, p-(1-n-propoxy-1,2,2-trimethylpropoxy)styrene, p-(1-i-propoxy-1,2,2-trimethylpropoxy)styrene, p-(1-n-butoxy-1,2,2-trimethylpropoxy)styrene, p-(1-t-butoxy-1,2,2-trimethylpropoxy)styrene, p-(1-n-pentyloxy-1,2,2-trimethylpropoxy)styrene, p-(1-n-hexyloxy-1,2,2-trimethylpropoxy)styrene, p-(1-cyclopentyloxy-1,2,2-trimethylpropoxy)styrene, p-(1-cyclohexyloxy-1,2,2-trimethylpropoxy)styrene, p-(1-benzyloxy-1,2,2-trimethylpropoxy)styrene and p-{1-(1'-naphthylmethoxy)-1,2,2-trimethylpropoxy}styrene; styrene-based monomers substituted by a linear, branched or cyclic alkoxycarbonyloxy group, such as p-methoxycarbonyloxystyrene, p-ethoxycarbonyloxystyrene, p-n-propyloxycarbonyloxystyrene, p-i-propyloxycarbonyloxystyrene, p-n-butoxycarbonyloxystyrene, p-2-methylpropoxycarbonyloxystyrene, p-1-methylpropoxycarbonyloxystyrene, p-t-butoxycarbonyloxystyrene and p-cyclohexyloxycarbonyloxystyrene; styrene-based monomers substituted by a linear, branched or cyclic alkoxycarbonylmethoxy group, such as p-methoxycarbonylmethoxystyrene, p-ethoxycarbonylmethoxystyrene, p-n-propyloxycarbonylmethoxystyrene, p-i-propyloxycarbonylmethoxystyrene, p-n-butoxycarbonylmethoxystyrene, p-2-methylpropoxycarbonylmethoxystyrene, p-1-methylpropoxycarbonylmethoxystyrene, p-t-butoxycarbonylmethoxystyrene and p-cyclohexyloxycarbonylmethoxystyrene; vinyl aromatic compounds such as 4-vinylphenylpropionic acid and 3-(4'-vinylphenyl)-1-propanol; unsaturated carboxylic acids or acid anhydrides thereof such as (meth)acrylic acid, maleic acid, fumaric acid, crotonic acid, mesaconic acid, citraconic acid, itaconic acid, maleic anhydride and citraconic anhydride; esters such as methyl ester, ethyl ester, n-propyl ester, i-propyl ester, n-butyl ester, 2-methylpropyl ester, 1-methylpropyl ester, t-butyl ester, n-pentyl ester, n-hexyl ester, cyclohexyl ester, 2-hydroxyethyl ester, 2-hydroxypropyl ester, 3-hydroxypropyl ester, 2,2-dimethyl-3-hydroxypropyl ester, benzyl ester, isobornyl ester, tricyclodecanyl ester, 1-adamantyl ester, 2-methyl-2-adamantyl ester, 2-ethyl-2-adamantyl ester, 2-n-propyladamantyl ester, 3-hydroxy-1-adamantyl ester, 2-methyl-3-hydroxy-1-adamantyl ester, 2-ethyl-3-hydroxy-1-adamantyl ester, 2-n-propyl-3-hydroxy-1-adamantyl ester, 2-i-propyl-1-adamantyl ester, 8-hydroxytetracyclododecane-3-methyl ester and 9-hydroxytetracyclododecane-3-methyl ester of the above unsaturated carboxylic acids; unsaturated nitriles such as (meth)acrylonitrile, maleinitrile, fumaronitrile, mesaconitrile, citraconitrile and itaconitrile; unsaturated amides such as (meth)acrylamide, N,N-dimethyl (meth)acrylamide, crotonamide, maleinamide, fumaramide, mesaconamide, citraconamide, itaconamide and N-(meth)acryloyl morpholine; unsaturated imides such as maleimide, N-phenylmaleimide and N-cyclohexylmaleimide; unsaturated alcohols such as (meth)allyl alcohols; and N-vinylaniline, vinylpyridines, N-vinyl-ε-caprolactam, N-vinylpyrrolidone, N-vinylimidazole and N-vinylcarbazole.

Out of these monofunctional monomers, preferred are styrene, p-hydroxystyrene, p-hydroxy-α-methylstyrene, p-t-butoxystyrene, p-(1-methoxyethoxy)styrene, p-(1-ethoxyethoxy)styrene, p-(1-cyclohexyloxyethoxy)styrene, p-(1-benzyloxyethoxy)styrene, p-{1-(1'-naphthylmethoxy)ethoxy)}styrene, p-(1-methoxypropoxy)styrene, p-(1-ethoxypropoxy)styrene, p-(1-benzyloxypropoxy)styrene, p-{1-(1'-naphthylmethoxy)propoxy)}styrene, p-(1-methoxy-1-methylethoxy)styrene, 4-vinylphenylpropionicacid, 3-(4'-vinylphenyl)-1-propanol, (meth)acrylic acid, t-butyl (meth)acrylate, 2-(meth)acryloyloxy-2-methyladamantane, 2-(meth)acryloyloxy-2-ethyladamantane, 1-(meth)acryloyloxy-3- hydroxyadamantane, 3-(meth)acryloyloxymethyl-8-hydroxytetracyclododecane, 3-(meth)acryloyloxymethyl-9-hydroxytetracyclododecane, N,N-dimethylacrylamide, N-acryloylmorpholine, N-vinyl-ε-caprolactam and N-vinylpyrrolidone.

The above monofunctional monomers may be used alone or in combination of two or more.

The content of the other recurring unit (α) in the polymer (A) is preferably 80 wt % or less, more preferably 5 to 70 wt %.

Polyfunctional monomers which provide the other recurring unit (β) include esters of a compound having two or more hydroxyl groups in the molecule, such as a polyhydric alcohol having two or more hydroxyl groups, polyether diol or polyester diol, and (meth)acrylic acid; adducts of a compound having two or more epoxy groups in the molecule typified by an epoxy resin and (meth)acrylic acid; and condensates of a compound having two or more amino groups in the molecule and (meth)acrylic acid. Specific examples of the polyfunctional monomers include ethylene glycol di(meth)acrylate, diethylene glycol di(meth)acrylate, triethylene glycol di(meth)acrylate, propylene glycol di(meth)acrylate, dipropylene glycol di(meth)acrylate, tripropylene glycol di(meth)acrylate, 1,4-butanediol di(meth)acrylate, trimethylolpropane di(meth)acrylate, trimethylolpropane tri(meth)acrylate, pentaerythritol tri(meth)acrylate, pentaerythritol tetra(meth)acrylate, 2,5-dimethyl-2,5-hexanediol di(meth)acrylate, tricyclodecanedimethanol di(meth)acrylate, di(meth)acrylates of a bisphenol A adduct with ethylene glycol or propylene glycol, epoxy (meth)acrylates such as (meth)acrylic acid bi-adduct of bisphenol A diglycidyl ether, and N,N'-methylenebis(meth)acrylamide.

Out of these polyfunctional monomers, ethylene glycol di(meth)acrylate, 2,5-dimethyl-2,5-hexanediol di(meth)acrylate, tricyclodecanedimethanol di(meth)acrylate and (meth)acrylic acid bi-adduct of bisphenol A diglycidyl ether are particularly preferred.

The above polyfunctional monomers may be used alone or in combination of two or more.

When the polymer (A) has the other recurring unit (β), a suitable crosslinking structure is introduced to reduce the mobility of a polymer molecular chain, thereby making it possible to suppress thermal deformation and improve heat resistance. When the crosslinking structure introduced by the polyfunctional monomer has acid dissociability, a reduction in molecular weight by exposure and the difference of dissolution speed in a developer between an exposed portion and an unexposed portion become larger than a linear resin or when the crosslinking structure has no acid dissociability, thereby making it possible to further improve resolution.

The content of the other recurring unit (β) in the polymer (A) is preferably 10 wt % or less, more preferably 7 wt % or less, particularly preferably 6 wt % or less.

The polymer (A) can be produced by selecting a monomer for the recurring unit (1) and optionally a monomer(s) for the other recurring unit (α) and/or the other recurring unit (β), as well as a suitable. radical polymerization initiator, in accordance with a suitable method such as bulk polymerization, solution polymerization, precipitation polymerization, emulsion polymerization, suspension polymerization or bulk-suspension polymerization, preferably solution polymerization.

Preferred examples of the radical polymerization initiator used for polymerization for the production of the polymer (A) include azobisisobutyronitrile and dimethyl-2,2'-azobis (2-methylpropionate). The reaction medium can be suitably selected from n-butyl acetate, tetrahydrofuran and propylene glycol monomethyl ether.

The polymerization conditions for producing the polymer (A) include a reaction temperature of preferably 50 to 90° C., more preferably 60 to 85° C. and a reaction time of preferably 3 to 10 hours.

The weight average molecular weight (to be referred to as "Mw" hereinafter) in terms of polystyrene measured by gel permeation chromatography (GPC) of the polymer (A) is 1,000 to 500,000. Mw of the polymer (A) depends on the existence of a crosslinking structure introduced by the polyfunctional monomer.

That is, Mw of the polymer (A) having no crosslinking structure introduced by the polyfunctional monomer is preferably 1,000 to 100,000, more preferably 3,000 to 40,000, particularly preferably 3,000 to 30,000. When Mw of the polymer (A) is less than 1,000, the sensitivity and heat resistance of the polymer as a resist lower and when Mw is more than 100,000, the solubility in a developer deteriorates.

The ratio (Mw/Mn) of Mw to the number average molecular weight (to be referred to as "Mn" hereinafter) in terms of polystyrene measured by gel permeation chromatography (GPC) of the polymer (A) having no crosslinking structure introduced by the polyfunctional monomer is preferably 1.0 to 5.0, more preferably 1.0 to 4.0, particularly preferably 1.0 to 3.0.

Mw of the polymer (A) having a crosslinking structure introduced by the polyfunctional monomer is preferably 3,000 to 500,000, more preferably 5,000 to 400,000, particularly preferably 8,000 to 300,000. When Mw of the polymer (A) is less than 3,000, the sensitivity and heat resistance of the polymer as a resist lower; and when Mw is more than 500,000, the developability of the polymer as a resist deteriorates.

Mw/Mn of the polymer (A) having a crosslinking structure introduced by the polyfunctional monomer is preferably 1.5 to 20.0, more preferably 1.5 to 15.0.

The polymer (A) has extremely low absorption of radiation and is very useful as a resin component of a radiation sensitive resin composition suitable for use as a chemically amplified resist. The radiation sensitive resin composition can reduce the difference of effective exposure amount between an upper portion and a lower portion of a resist film, can retain the rectangularity of even a fine pattern and has high sensitivity (small amount of exposure energy).

(B) Radiation Sensitive Acid Generating Agent

The radiation sensitive resin composition of the present invention comprises the above polymer (A) and (B) a radiation sensitive acid generating agent (to be referred to as "acid generating agent (B)" hereinafter) which generates an acid upon exposure.

The acid generating agent (B) is selected from (1) an onion salt, (2) sulfone compound, (3) sulfonate compound, (4) sulfonyloxyimide compound, (5) disulfonyldiazomethane compound and (6) disulfonylmethane derivative.

Examples of the above acid generating agents (B) are given below.
(1) Onium Salt:

The onium salt is, for example, an iodonium salt, sulfonium salt (including a tetrahydrothiophenium salt), phosphonium salt, diazonium salt, ammonium salt or pyridinium salt.

Illustrative examples of the onium salt include bis(4-t-butylphenyl)iodonium trifluoromethanesulfonate, bis(4-t- butylphenyl)iodonium nonafluoro-n-butanesulfonate, bis(4-t-butylphenyl)iodonium perfluoro-n-octanesulfonate, bis(4-t-butylphenyl)iodonium pyrenesulfonate, bis(4-t-butylphenyl)iodonium n-dodecylbenzenesulfonate, bis(4-t-butylphenyl)iodonium p-toluenesulfonate, bis(4-t-butylphenyl)iodonium benzenesulfonate, bis(4-t-butylphenyl)iodonium 10-camphorsulfonate, bis(4-t-butylphenyl)iodonium n-octanesulfonate, bis(4-t-butylphenyl)iodonium 2-trifluoromethylbenzenesulfonate, bis(4-t-butylphenyl) 4-trifluoromethylbenzenesulfonate, bis(4-t-butylphenyl)iodonium perfluorobenzenesulfonate, diphenyliodonium trifluoromethanesulfonate, diphenyliodonium nonafluoro-n-butanesulfonate, diphenyliodonium perfluoro-n-octanesulfonate, diphenyliodonium pyrenesulfonate, diphenyliodonium n-dodecylbenzenesulfonate, diphenyliodonium p-toluenesulfonate, diphenyliodonium benzenesulfonate, diphenyliodonium 10-camphorsulfonate, diphenyliodonium n-octanesulfonate, diphenyliodonium 2-trifluoromethylbenzenesulfonate, diphenyliodonium 4-trifluoromethylbenzenesulfonate, diphenyliodonium perfluorobenzenesulfonate, di(p-toluyl)iodonium trifluoromethanesulfonate, di(p-toluyl)iodonium nonafluoro-n-butanesulfonate, di(p-toluyl)iodonium perfluoro-n-octanesulfonate, di(p-toluyl)iodoniumpyrenesulfonate, di(p-toluyl)iodonium n-dodecylbenzenesulfonate, di(p-toluyl)iodonium p-toluenesulfonate, di(p-toluyl)iodoniumbenzenesulfonate, di(p-toluyl)iodonium 10-camphorsulfonate, di(p-toluyl)iodonium n-octanesulfonate, di(p-toluyl)iodonium 2-trifluoromethylbenzenesulfonate, di(p-toluyl)iodonium 4-trifluoromethylbenzenesulfonate, di(p-toluyl)iodonium perfluorobenzenesulfonate, di(3,4-dimethylphenyl)iodonium trifluoromethanesulfonate, di(3,4-dimethylphenyl)iodonium nonafluoro-n-butanesulfonate, di(3,4-dimethylphenyl)iodonium perfluoro-n-octanesulfonate, di(3,4-dimethylphenyl)iodonium pyrenesulfonate, di(3,4-dimethylphenyl)iodonium n-dodecylbenzenesulfonate, di(3,4-dimethylphenyl)iodonium p-toluenesulfonate, di(3,4-dimethylphenyl)iodonium benzenesulfonate, di(3,4-dimethylphenyl)iodonium 10-camphorsulfonate, di(3,4-dimethylphenyl)iodonium n-octanesulfonate, di(3,4-dimethylphenyl)iodonium 2-trifluoromethylbenzenesulfonate, di(3,4-dimethylphenyl)iodonium 4-trifluoromethylbenzenesulfonate, di(3,4-dimethylphenyl)iodonium perfluorobenzenesulfonate, p-nitrophenyl phenyliodonium trifluoromethanesulfonate, p-nitrophenyl phenyliodonium nonafluoro-n-butanesulfonate, p-nitrophenyl phenyliodonium perfluoro-n-octanesulfonate, p-nitrophenyl phenyliodonium pyrenesulfonate, p-nitrophenyl phenyliodonium n-dodecylbenzenesulfonate, p-nitrophenyl phenyliodonium p-toluenesulfonate, p-nitrophenyl phenyliodonium benzenesulfonate, p-nitrophenyl phenyliodonium 10-camphorsulfonate, p-nitrophenyl phenyliodonium n-octanesulfonate, p-nitrophenyl phenyliodonium 2-trifluoromethylbenzenesulfonate, p-nitrophenyl phenyliodonium 4-trifluoromethylbenzenesulfonate, p-nitrophenyl phenyliodonium perfluorobenzenesulfonate, di(3-nitrophenyl)iodonium trifluoromethanesulfonate, di(3-nitrophenyl)iodonium nonafluoro-n-butanesulfonate, di(3-nitrophenyl)iodonium perfluoro-n-octanesulfonate, di(3-nitrophenyl)iodonium pyrenesulfonate, di(3-nitrophenyl)iodonium n-dodecylbenzenesulfonate, di(3-nitrophenyl)iodonium p-toluenesulfonate, di(3-nitrophenyl)iodonium benzenesulfonate, di(3-nitrophenyl)iodonium 10-camphorsulfonate, di(3-nitrophenyl)iodonium n-octanesulfonate, di(3-nitrophenyl)iodonium 2-trifluoromethylbenzenesulfonate, di(3-nitrophenyl)iodonium 4-trifluoromethylbenzenesulfonate, di(3-nitrophenyl)iodonium perfluorobenzenesulfonate, 4-methoxyphenyl phenyliodonium trifluoromethanesulfonate, 4-methoxyphenyl phenyliodonium nonafluoro-n-butanesulfonate, 4-methoxyphenyl phenyliodonium perfluoro-n-octanesulfonate, 4-methoxyphenyl phenyliodonium pyrenesulfonate, 4-methoxyphenyl phenyliodonium n-dodecylbenzenesulfonate, 4-methoxyphenyl phenyliodonium p-toluenesulfonate, 4-methoxyphenyl phenyliodonium benzenesulfonate, 4-methoxyphenyl phenyliodonium 10-camphorsulfonate, 4-methoxyphenyl phenyliodonium n-octanesulfonate, 4-methoxyphenyl phenyliodonium 2-trifluoromethylbenzenesulfonate, 4-methoxyphenyl phenyliodonium 4-trifluoromethylbenzenesulfonate, 4-methoxyphenyl phenyliodonium perfluorobenzenesulfonate, di(4-chlorophenyl)iodonium trifluoromethanesulfonate, di(4-chlorophenyl)iodonium nonafluoro-n-butanesulfonate, di(4-chlorophenyl)iodonium perfluoro-n-octanesulfonate, di(4-chlorophenyl)iodonium pyrenesulfonate, di(4-chlorophenyl)iodonium n-dodecylbenzenesulfonate, di(4-chlorophenyl)iodonium p-toluenesulfonate, di(4-chlorophenyl)iodonium benzenesulfonate, di(4-chlorophenyl)iodonium 10-camphorsulfonate, di(4-chlorophenyl)iodonium n-octanesulfonate, di(4-chlorophenyl)iodonium 2-trifluoromethylbenzenesulfonate, di(4-chlorophenyl)iodonium 4-trifluoromethylbenzenesulfonate, di(4-chlorophenyl)iodonium perfluorobenzenesulfonate, di(4-trifluoromethylphenyl)iodonium trifluoromethanesulfonate, di(4-trifluoromethylphenyl)iodonium nonafluoro-n-butanesulfonate, di(4-trifluoromethylphenyl)iodonium perfluoro-n-octanesulfonate, di(4-trifluoromethylphenyl)iodonium pyrenesulfonate, di(4-trifluoromethylphenyl)iodonium n-dodecylbenzenesulfonate, di(4-trifluoromethylphenyl)iodonium p-toluenesulfonate, di(4-trifluoromethylphenyl)iodonium benzenesulfonate, di(4-trifluoromethylphenyl)iodonium 10-camphorsulfonate, di(4-trifluoromethylphenyl)iodonium n-octanesulfonate, di(4-trifluoromethylphenyl)iodonium 2-trifluoromethylbenzenesulfonate, di(4-trifluoromethylphenyl)iodonium 4-trifluoromethylbenzenesulfonate, di(4-trifluoromethylphenyl)iodonium perfluorobenzenesulfonate, di(1-naphthyl)iodonium trifluoromethanesulfonate, di(1-naphthyl)iodonium nonafluoro-n-butanesulfonate, di(1-naphthyl)iodonium perfluoro-n-octanesulfonate, di(1-naphthyl)iodonium pyrenesulfonate, di(1-naphthyl)iodonium n-dodecylbenzenesulfonate, di(1-naphthyl)iodonium p-toluenesulfonate, di(1-naphthyl)iodonium benzenesulfonate, di(1-naphthyl)iodonium 10-camphorsulfonate, di(1-naphthyl)iodonium n-octanesulfonate, di(1-naphthyl)iodonium 2-trifluoromethylbenzenesulfonate, di(1-naphthyl)iodonium 4-trifluoromethylbenzenesulfonate, di(1-naphthyl)iodonium perfluorobenzenesulfonate, biphenyleneiodonium trifluoromethanesulfonate, biphenyleneiodonium nonafluoro-n-butanesulfonate, biphenyleneiodonium perfluoro-n-octanesulfonate, biphenyleneiodonium pyrenesulfonate, biphenyleneiodonium n-dodecylbenzenesulfonate, biphenyleneiodonium p-toluenesulfonate, biphenyleneiodonium benzenesulfonate, biphenyleneiodonium 10-camphorsulfonate, biphenyleneiodoniumn-octanesulfonate, biphenyleneiodonium 2-trifluoromethylbenzenesulfonate, biphenyleneiodonium 4-trifluoromethylbenzenesulfonate, biphenyleneiodonium perfluorobenzenesulfonate, 2-chlorobiphenyleneiodonium trifluoromethanesulfonate, 2-chlorobiphenyleneiodonium nonafluoro-n-butanesulfonate, 2-chlorobiphenyleneiodonium perfluoro-n-octanesulfonate, 2-chlorobiphenyleneiodonium pyrenesulfonate, 2-chlorobiphenyleneiodonium n-dodecylbenzenesulfonate, 2-chlorobiphenyleneiodonium p-toluenesulfonate, 2-chlorobiphenyleneiodonium benzenesulfonate, 2-chlorobiphenyleneiodonium 10-camphorsulfonate, 2-chlorobiphenyleneiodohium n-octanesulfonate, 2-chlorobiphenyleneiodonium 2-trifluoromethylbenzenesulfonate, 2-chlorobiphenyleneiodonlum 4-trifluoromethylbenzenesulfonate, 2-chlorobiphenyleneiodonium perfluorobenzenesulfonate, triphenylsulfonium trifluoromethanesulfonate, triphenylsulfonium nonafluoro-n-butanesulfonate, triphenylsulfonium perfluoro-n-octanesulfonate, triphenylsulfonium pyrenesulfonate, triphenylsulfonium n-dodecylbenzenesulfonate, triphenylsulfonium p-toluenesulfonate, triphenylsulfonium benzenesulfonate, triphenylsulfonium 10-camphorsulfonate, triphenylsulfonium n-octanesulfonate, triphenylsulfoonium 2-trifluoromethylbenzenesulfonate, triphenylsulfonium 4-trifluoromethylbenzenesulfonate, triphenylsulfonium 1-naphthalenesulfonate, triphenylsulfonium perfluorobenzenesulfonate, triphenylsulfonium hexafluoroantimonate, 4-t-butylphenyl diphenylsulfonium trifluoromethanesulfonate, 4-t-butylphenyl diphenylsulfonium nonafluoro-n-butanesulfonate, 4-t-butylphenyl diphenylsulfonium perfluoro-n-octanesulfonate, 4-t-butylphenyl diphenyisulfonium pyrenesulfonate, 4-t-butylphenyl diphenylsulfonium n-dodecylbenzenesulfonate, 4-t-butylphenyl diphenylsulfonium p-toluenesulfonate, 4-t-butylphenyl diphenylsulfonium benzenesulfonate, 4-t-butylphenyl diphenylsulfonium 10-cam phorsulfonate, 4-t-butylphenyl diphenylsulfonium n-octanesulfonate, 4-t-butylphenyl diphenylsulfonium 2-trifluoromethylbenzenesulfonate, 4-t-butylphenyl diphenylsulfonium 4-trifluoromethylbenzenesulfonate, 4-t-butylphenyl diphenylsulfonium perfluorobenzenesulfonate, 4-t-butoxyphenyl diphenylsulfonium trifluoromethanesulfonate, 4-t-butoxyphenyl diphenylsulfonium nonafluoro-n-butanesulfonate, 4-t-butoxyphenyl diphenylsulfonium perfluoro-n-octanesulfonate, 4-t-butoxyphenyl diphenylsulfonium pyrenesulfonate, 4-t-butoxyphenyl diphenylsulfonium n-dodecylbenzenesulfonate, 4-t-butoxyphenyl diphenylsulfonium p-toluenesulfonate, 4-t-butoxyphenyl diphenylsulfonium benzenesulfonate, 4-t-butoxyphenyl diphenylsulfonium 10-camphorsulfonate, 4-t-butoxyphenyl diphenylsulfonium n-octanesulfonate, 4-t-butoxyphenyl diphenylsulfonium 2-trifluoromethylbenzenesulfonate, 4-t-butoxyphenyl diphenylsulfonium 4-trifluoromethylbenzenesulfonate, 4-t-butoxyphenyl diphenylsulfonium perfluorobenzenesulfonate, 4-hydroxyphenyl diphenylsulfonium trifluoromethanesulfonate, 4-hydroxyphenyl diphenylsulfonium nonafluoro-n-butanesulfonate, 4-hydroxyphenyl diphenylsulfonium perfluoro-n-octanesulfonate, 4-hydroxyphenyl diphenylsulfonium pyrenesulfonate, 4-hydroxyphenyl diphenylsulfonium n-dodecylbenzenesulfonate, 4-hydroxyphenyl diphenylsulfonium p-toluenesulfonate, 4-hydroxyphenyl diphenylsulfonium benzenesulfonate, 4-hydroxyphenyl diphenylsulfonium 10-camphorsulfonate, 4-hydroxyphenyl diphenylsulfonium n-octanesulfonate, 4-hydroxyphenyl diphenylsulfonium 2-trifluoromethylbenzenesulfonate, 4-hydroxyphenyl diphenylsulfonium 4-trifluoromethylbenzenesulfonate, 4-hydroxyphenyl diphenylsulfonium perfluorobenzenesulfonate, tri(4-methoxyphenyl)sulfonium trifluoromethanesulfonate, tri(4-methoxyphenyl)sulfonium nonafluoro-n-butanesulfonate, tri(4-methoxyphenyl)sulfonium perfluoro-n-octanesulfonate, tri(4-methoxyphenyl)sulfonium pyrenesulfonate, tri(4-methoxyphenyl)sulfonium n-dodecylbenzenesulfonate, tri(4-methoxyphenyl)sulfonium p-toluenesulfonate, tri(4-methoxyphenyl)sulfonium benzenesulfonate, tri(4-methoxyphenyl)sulfonium 10-camphorsulfonate, tri(4-methoxyphenyl)sulfonium n-octanesulfonate, tri(4-methoxyphenyl)sulfonium 2-trifluoromethylbenzenesulfonate, tri(4-methoxyphenyl) sulfonium 4-trifluoromethylbenzenesulfonate, tri(4-methoxyphenyl)sulfonium perfluorobenzenesulfonate, di(4-methoxyphenyl) p-toluylsulfonium trifluoromethanesulfonate, di(4-methoxyphenyl) p-toluylsulfonium nonafluoro-n-butanesulfonate, di(4-methoxyphenyl) p-toluylsulfonium perfluoro-n-octanesulfonate, di(4-methoxyphenyl) p-toluylsulfonium pyrenesulfonate, di(4-methoxyphenyl) p-toluylsulfonium n-dodecylbenzenesulfonate, di(4-methoxyphenyl) p-toluylsulfonium p-toluenesulfonate, di(4-methoxyphenyl) p-toluylsulfonium benzenesulfonate, di(4-methoxyphenyl) p-toluylsulfonium 10-camphorsulfonate, di(4-methoxyphenyl) p-toluylsulfonium n-octanesulfonate, di(4-methoxyphenyl) p-toluylsulfonium 2-trifluoromethylbenzenesulfonate, di(4-methoxyphenyl) p-toluylsulfonium 4-trifluoromethylbenzenesulfonate, di(4-methoxyphenyl) p-toluylsulfonium perfluorobenzenesulfonate, phenyl tetramethylenesulfonium trifluoromethanesulfonate, phenyl tetramethylenesulfonium nonafluoro-n-butanesulfonate, phenyl tetramethylenesulfonium perfluoro-n-octanesulfonate, phenyl tetramethylenesulfonium pyrenesulfonate, phenyl tetramethylenesulfonium n-dodecylbenzenesulfonate, phenyl tetramethylenesulfonium p-toluenesulfonate, phenyl tetramethylenesulfonium benzenesulfonate, phenyl tetramethylenesulfonium 10-camphorsulfonate, phenyl tetramethylenesulfonium n-octanesulfonate, phenyl tetramethylenesulfonium 2-trifluoromethylbenzenesulfonate, phenyl tetramethylenesulfonium 4-trifluoromethylbenzenesulfonate, phenyl tetramethylenesulfonium perfluorobenzenesulfonate, 4-hydroxyphenyl tetramethylenesulfonium trifluoromethanesulfonate, 4-hydroxyphenyl tetramethylenesulfonium nonafluoro-n-butanesulfonate, 4-hydroxyphenyl tetramethylenesulfonium perfluoro-n-octanesulfonate, 4-hydroxyphenyl tetramethylenesulfonium pyrenesulfonate, 4-hydroxyphenyl tetramethylenesulfonium n-dodecylbenzenesulfonate, 4-hydroxyphenyl tetramethylenesulfonium p-toluenesulfonate, 4-hydroxyphenyl tetramethylenesulfonium benzenesulfonate, 4-hydroxyphenyl tetramethylenesulfonium 10-camphorsulfonate, 4-hydroxyphenyl tetramethylenesulfonium n-octanesulfonate, 4-hydroxyphenyl tetramethylenesulfonium 2-trifluoromethylbenzenesulfonate, 4-hydroxyphenyl tetramethylenesulfonium 4-trifluoromethylbenzenesulfonate, 4-hydroxyphenyl tetramethylenesulfonium perfluorobenzenesulfonate, phenyl biphenylenesulfonium trifluoromethanesulfonate, phenyl biphenylenesulfonium nonafluoro-n-butanesulfonate, phenyl biphenylenesulfonium perfluoro-n-octanesulfonate, phenyl biphenylenesulfonium pyrenesulfonate, phenyl biphenylenesulfonium n-dodecylbenzenesulfonate, phenyl biphenylenesulfonium p-toluenesulfonate, phenyl biphenylenesulfonium benzenesulfonate, phenyl biphenylenesulfonium 10-camphorsulfonate, phenyl biphenylenesulfonium n-octanesulfonate, phenyl biphenylenesulfonium 2-trifluoromethylbenzenesulfonate, phenyl biphenylenesulfonium 4-trifluoromethylbenzenesulfonate, phenyl biphenylenesulfonium perfluorobenzenesulfonate, (4-phenylthiophenyl) diphenylsulfonium trifluoromethanesulfonate, (4-phenylthiophenyl) diphenylsulfonium nonafluoro-n-butanesulfonate, (4-phenylthiophenyl) diphenylsulfonium perfluoro-n-octanesulfonate, (4-phenylthiophenyl) diphenylsulfonium pyrenesulfonate, (4-phenylthiophenyl) diphenylsulfonium n-dodecylbenzenesulfonate, (4-phenylthiophenyl) diphenylsulfonium p-toluenesulfonate, (4-phenylthiophenyl) diphenylsulfonium benzenesulfonate, (4-phenylthiophenyl) diphenylsulfonium 10-camphorsulfonate, (4-phenylthiophenyl) diphenylsulfonium n-octanesulfonate, (4-phenylthiophenyl) diphenylsulfonium 2-trifluoromethylbenzenesulfonate, (4-phenylthiophenyl) diphenylsulfonium 4-trifluoromethylbenzenesulfonate, (4-phenylthiophenyl) diphenylsulfonium perfluorobenzenesulfonate, 4,4'-bis(diphenylsulfoniophenyl)sulfide di(trifluoromethanesulfonate), 4,4'-bis(diphenylsulfoniophenyl)sulfide di(nonafluoro-n-butanesulfonate), 4,4'-bis(diphenylsulfoniophenyl)sulfide di(perfluoro-n-octanesulfonate), 4,4'-bis(diphenylsulfoniophenyl)sulfide di(pyrenesulfonate), 4,4'-bis(diphenylsulfoniophenyl)sulfide di(n-dodecylbenzenesulfonate), 4,4'-bis(diphenylsulfoniophenyl)sulfide di(p-toluenesulfonate), 4,4'-bis(diphenylsulfoniophenyl)sulfide di(benzenesulfonate), 4,4'-bis(diphenylsulfoniophenyl)sulfide di(10-camphorsulfonate), 4,4'-bis(diphenylsulfoniophenyl)sulfide di(n-octanesulfonate), 4,4'-bis(diphenylsulfoniophenyl)sulfide di(2-trifluoromethylbenzenesulfonate), 4,4'-bis(diphenylsulfoniophenyl)sulfide di(4-trifluoromethylbenzenesulfonate), 4,4'-bis(diphenylsulfoniophenyl)sulfide di(perfluorobenzenesulfonate), 4-hydroxy-1-naphthyltetrahydrothiophenium trifluoromethanesulfonate, 4-methoxy-1-naphthyltetrahydrothiophenium trifluoromethanesulfonate, 4-ethoxy-1-naphthyltetrahydrothiophenium trifluoromethanesulfonate, 4-n-propoxy-1-naphthyltetrahydrothiophenium trifluoromethanesulfonate, 4-n-butoxy-1-naphthyltetrahydrothiophenium trifluoromethanesulfonate, 4-methoxymethoxy-1-naphthyltetrahydrothiophenium trifluoromethanesulfonate, 4-ethoxymethoxy-1-naphthyltetrahydrothiophenium trifluoromethanesulfonate, 4-(1'-methoxyethoxy)-1-naphthyltetrahydrothiophenium trifluoromethanesulfonate, 4-(2'-methoxyethoxy)-1-naphthyltetrahydrothiophenium trifluoromethanesulfonate, 4-methoxycarbonyloxy-1-naphthyltetrahydrothiophenium trifluoromethanesulfonate, 4-ethoxycarbonyloxy-1-naphthyltetrahydrothiophenium trifluoromethanesulfonate, 4-n-propoxycarbonyloxy-1-naphthyltetrahydrothiophenium trifluoromethanesulfonate, 4-i-propoxycarbonyloxy-1-naphthyltetrahydrothiophenium trifluoromethanesulfonate, 4-n-butoxycarbonyloxy-1-naphthyltetrahydrothiophenium trifluoromethanesulfonate, 4-t-butoxycarbonyloxy-1-naphthyltetrahydrothiophenium trifluoromethanesulfonate, 4-(2'-tetrahydrofuranyloxy)-1-naphthyl tetrahydrothiophenium trifluoromethanesulfonate, 4-(2'-tetrahydropyranyloxy)-1-naphthyl tetrahydrothiophenium trifluoromethanesulfonate, 4-benzyloxy-1-naphthyltetrahydrothiophenium trifluoromethanesulfonate and 1-(naphthylacetomethyl)tetrahydrothiophenium trifluoromethanesulfonate.

(2) Sulfone Compound:
The sulfone compound is, for example, β-ketosulfone, β-sulfonylsulfone or α-diazo compound thereof.
Illustrative examples of the sulfone compound include phenacyl phenyl sulfone, mesityl phenacyl sulfone, bis(phenylsulfonyl)methane and 4-trisphenacyl sulfone.

(3) Sulfonate Compound:
The sulfonate compound is, for example, alkyl sulfonate, haloalkyl sulfonate, aryl sulfonate or iminosulfonate.
Illustrative examples of the sulfonate compound include benzoin tosylate, pyrogallol tris(trifluoromethanesulfonate), pyrogallol tris(nonafluoro-n-butanesulfonate), pyrogallol tris(methanesulfonate), nitrobenzyl-9,10-diethoxyanthracene-2-sulfonate, α-methylolbenzoin tosylate, α-methylolbenzoin n-octanesulfonate, α-methylolbenzoin trifluoromethanesulfonate and α-methylolbenzoin n-dodecanesulfonate.

(4) Sulfonyloxyimide Compound:
The sulfonyloxyimide compound is, for example, a compound represented by the following formula (8):

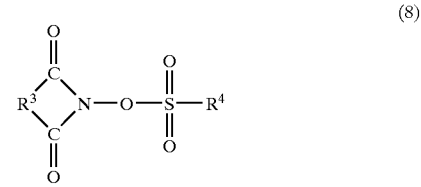

(8)

wherein $R^3$ is a divalent group such as a linear, branched or cyclic alkylene group, arylene group or alkoxylene group, and $R^4$ is a monovalent group such as a linear, branched or cyclic alkyl group, aryl group, linear, branched or cyclic halogen-substituted alkyl group or halogen-substituted aryl group.

Illustrative examples of the sulfonyloxyimide compound include N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hept-5-ene-2,3-dicarboxyimide, N-(trifluoromethylsulfonyloxy)-7-oxabicyclo[2.2.1]hept-5-ene-2,3-dicarboxyimide, N-(trifluoromethylsulfonyloxy)bicyclo[2.2.]heptan-5,6-oxy-2,3-dicarboxyimide, N-(trifluoromethylsulfonyloxy)naphthylimide, N-(10-camphorsulfonyloxy)succinimide, N-(10-camphorsulfonyloxy)phthalimide, N-(10-camphorsulfonyloxy)diphenylmaleimide, N-(10-camphorsulfonyloxy)bicyclo[2.2.1]hept-5-ene-2,3-dicarboxyimide, N-(10-camphorsulfonyloxy)-7-oxabicyclo[2.2.1]hept-5-ene-2,3-dicarboxyimide, N-(10-camphorsulfonyloxy)bicyclo[2.2.1]heptane-5,6-oxy-2,3-dicarboxyimide, N-(10-camphorsulfonyloxy)naphthylimide, N-(n-octanesulfonyloxy)succinimide, N-(n-octanesulfonyloxy)phthalimide, N-(n-octanesulfonyloxy)diphenylmaleimide, N-(n-octanesulfonyloxy)bicyclo[2.2.1]hept-5-ene-2,3-dicarboxyimide, N-(n-octanesulfonyloxy)-7-oxabicyclo[2.2.1]hept-5-ene-2,3-dicarboxyimide, N-(n-octanesulfonyloxy)bicyclo[2.2.1]heptane-5,6-oxy-2,3-dicarboxyimide, N-(n-octanesulfonyloxy)naphthylimide, N-(p-toluenesulfonyloxy)succinimide, N-(p-toluenesulfonyloxy)phthalimide, N-(p-toluenesulfonyloxy)diphenylmaleimide, N-(p-toluenesulfonyloxy)bicyclo[2.2.1]hept-5-ene-2,3-dicarboxyimide, N-(p-toluenesulfonyloxy)-7-oxabicyclo[2.2.1]hept-5-ene-2,3-dicarboxyimide, N-(p-toluenesulfonyloxy)bicyclo[2.2.1]heptane-5,6-oxy-2,3-dicarboxyimide, N-(p-toluenesulfonyloxy)naphthylimide, N-(2- trifluoromethylbenzenesulfonyloxy)succinimide, N-(2-trifluoromethylbenzenesulfonyloxy)phthalimide, N-(2-trifluoromethylbenzenesulfonyloxy)diphenylmaleimide, N-(2-trifluoromethylbenzenesulfonyloxy)bicyclo[2.2.1]hept-5-ene-2,3-dicarboxyimide, N-(2-trifluoromethylbenzenesulfonyloxy)-7-oxabicyclo[2.2.1]hept-5-ene-2,3-dicarboxyimide, N-(2-trifluoromethylbenzenesulfonyloxy)bicyclo[2.2.1]heptane-5,6-oxy-2,3-dicarboxyimide, N-(2-trifluoromethylbenzenesulfonyloxy)naphthylimide, N-(4-trifluoromethylbenzenesulfonyloxy)succinimide, N-(4-trifluoromethylbenzenesulfonyloxy)phthalimide, N-(4-trifluoromethylbenzenesulfonyloxy)diphenylmaleimide, N-(4-trifluoromethylbenzenesulfonyloxy)bicyclo[2.2.1]hept-5-ene-2,3-dicarboxyimide, N-(4-trifluoromethylbenzenesulfonyloxy)-7-oxabicyclo[2.2.1]hept-5-ene-2,3-dicarboxyimide, N-(4-trifluoromethylbenzenesulfonyloxy)bicyclo[2.2.1]heptane-5,6-oxy-2,3-dicarboxyimide, N-(4-trifluoromethylbenzenesulfonyloxy)naphthylimide, N-(perfluorobenzenesulfonyloxy)succinimide, N-(perfluorobenzenesulfonyloxy)phthalimide, N-(perfluorobenzenesulfonyloxy)diphenylmaleimide, N-(perfluorobenzenesulfonyloxy)bicyclo[2.2.1]hept-5-ene-2,3-dicarboxyimide, N-(perfluorobenzenesulfonyloxy)-7-oxabicyclo[2.2.1]hept-5-ene-2,3-dicarboxyimide, N-(perfluorobenzenesulfonyloxy)bicyclo[2.2.1]heptane-5,6-oxy-2,3-dicarboxyimide, N-(perfluorobenzenesulfonyloxy)naphthylimide, N-(1-naphthalenesulfonyloxy)succinimide, N-(1-naphthalenesulfonyloxy)phthalimide, N-(1-naphthalenesulfonylbxy)diphenylmaleimide, N-(1-naphthalenesulfonyloxy)bicyclo[2.2.1]hept-5-ene-2,3-dicarboxyimide, N-(1-naphthalenesulfonyloxy)-7-oxabicyclo[2.2.1]hept-5-ene-2,3-dicarboxyimide, N-(1-naphthalenesulfonyloxy)bicyclo[2.2.1]heptane-5,6-oxy-2,3-dicarboxyimide, N-(1-naphthalenesulfonyloxy)naphthylimide, N-(nonafluoro-n-butanesulfonyloxy)succinimide, N-(nonafluoro-n-butanesulfonyloxy)phthalimide, N-(nonafluoro-n-butanesulfonyloxy)diphenylmaleimide, N-(nonafluoro-n-butanesulfonyloxy)bicyclo[2.2.1]hept-5-ene-2,3-dicarboxyimide, N-(nonafluoro-n-butanesulfonyloxy)-7-oxabicyclo[2.2.1]hept-5-ene-2,3-dicarboxyimide, N-(nonafluoro-n-butanesulfonyloxy)bicyclo[2.2.]heptane-5,6-oxy-2,3-dicarboxyimide, N-(nonafluoro-n-butanesulfonyloxy)naphthylimide, N-(perfluoro-n-octanesulfonyloxy)succinimide, N-(perfluoro-n-octanesulfonyloxy)phthalimide, N-(perfluoro-n-octanesulfonyloxy)diphenylmaleimide, N-(perfluoro-n-octanesulfonyloxy)bicyclo[2.2.1]hept-5-ene-2,3-dicarboxyimide, N-(perfluoro-n-octanesulfonyloxy)-7-oxabicyclo[2.2.1]hept-5-ene-2,3-dicarboxyimide, N-(perfluoro-n-octanesulfonyloxy)bicyclo[2.2.1]heptane-5,6-oxy-2,3-dicarboxyimide, N-(perfluoro-n-octanesulfonyloxy)naphthylimide, N-(benzenesulfonyloxy)succinimide, N-(benzenesulfonyloxy)phthalimide, N-(benzenesulfonyloxy)diphenylmaleimide, N-(benzenesulfonyloxy)bicyclo[2.2.]hept-5-ene-2,3-dicarboxyimide, N-(benzenesulfonyloxy)-7-oxabicyclo[2.2.1]hept-5-ene-2,3-dicarboxyimide, N-(benzenesulfonyloxy)bicyclo[2.2.1]heptane-5,6-oxy-2,3-dicarboxyimide and N-(benzenesulfonyloxy)naphthylimide.

(5) Disulfonyldiazomethane Compound:

The disulfonyldiazomethane compound is, for example, a compound represented by the following formula (9):

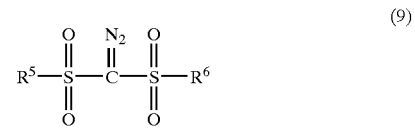

(9)

wherein $R^5$ and $R^6$ are each independently a monovalent group such as a linear, branched or cyclic alkyl group, aryl group, linear, branched or cyclic halogen-substituted alkyl group or halogen-substituted aryl group.

Illustrative examples of the disulfonyldiazomethane compound include bis (trifluoromethylsulfonyl) diazomethane, bis(cyclohexylsulfonyl)diazomethane, bis(phenylsulfonyl) diazomethane, bis(p-toluenesulfonyl)diazomethane, bis(2,4-dimethylphenylsulfonyl)diazomethane, methylsulfonyl p-toluenesulfonyldiazomethane, bis(4-t-butylphenylsulfonyl)diazomethane, bis(4-chlorophenylsulfonyl)diazomethane, cyclohexylsulfonyl p-toluenesulfonyldiazomethane, 1-cyclohexylsulfonyl 1-(1',1'-dimethylethylsulfonyl)diazomethane, bis(1,1-dimethylethylsulfpnyl)diazomethane, bis(1-methylethylsulfonyl)diazomethane, bis(3,3-dimethyl-1,5-dioxaspiro[5.5]dodecane-8-sulfonyl) diazomethane and bis (1,4-dioxaspiro[4.5]decane-7-sulfonyl)diazomethane.

(6) Disulfonylmethane Derivative:

The disulfonylmethane derivative is, for example, a compound represented by the following formula (10):

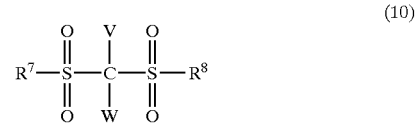

(10)

wherein $R^7$ and $R^8$ are each independently a monovalent linear or branched aliphatic hydrocarbon group, cycloalkyl group, aryl group, aralkyl group or monovalent other organic group having a hetero atom, V and W are each independently an aryl group, hydrogen atom, monovalent linear or branched aliphatic hydrocarbon group or monovalent other organic group having a hetero atom, and at least one of V and W is an aryl group, or V and W are bonded together to form a single ring or multiple rings having at least one unsaturated bond, or V and W are bonded together to form a group represented by the following formula:

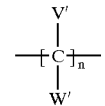

wherein V' and W' are each independently a hydrogen atom, halogen atom, linear or branched alkyl group, cycloalkyl group, aryl group or aralkyl group, or V' and W' bonded to the same or different carbon atoms are bonded together to form a carbon-single ring structure, with the proviso that V's and W's may be the same or different, and n is an integer of 2 to 10.

Out of these acid generating agents (B), (1) onium salts, (2) sulfonyloxyimide compounds and (6) disulfonylmethane derivatives are preferred and bis(4-t-butylphenyl)iodonium nonafluoro-n-butanesulfonate, bis(4-t-butylphenyl) iodonium 10-camphorsulfonate, triphenylsulfonium trifluoromethanesulfonate, N-(trifluoromethylsulfonyloxy) bicyclo[2.2.1]hept-5-ene-2,3-dicarboxyimide and bis(1,4- dioxaspiro[4.5]decane-7-sulfonyl)diazomethane are particularly preferred.

The above acid generating agents (B) may be used alone or in combination of two or more.

In the present invention, the amount of the acid generating agent (B) is preferably 0.1 to 20 parts by weight, more preferably 0.5 to 15 parts by weight based on 100 parts by weight of the polymer (A).

Preferably, the radiation sensitive resin composition of the present invention further comprises an acid diffusion control agent which has the function of controlling such a phenomenon that an acid generated from the acid generating agent (B) by exposure is dispersed in a resist film in order to suppress an unfavorable chemical reaction in an unexposed area.

By using this acid diffusion control agent, the storage stability of the composition and the resolution of the composition as a resist can be improved and changes in the line width of the resist pattern caused by fluctuations in PED can be further suppressed, thereby making it possible to obtain very excellent process stability.

The acid diffusion control agent is preferably a nitrogen-containing organic compound whose basicity is not changed by exposure or a heat treatment in the step of forming a resist pattern.

The nitrogen-containing organic compound is a compound represented by the following formula (11):

(11)

wherein $R^9$, $R^{10}$ and $R^{11}$ are each independently a hydrogen atom, linear, branched or cyclic alkyl group, aryl group or aralkyl group all of which may be substituted by a functional group such as a hydroxy group (to be referred to as "nitrogen-containing compound (I)" hereinafter), diamino compound having two nitrogen atoms in the molecule (to be referred to as "nitrogen-containing compound (II)" hereinafter), polyamino polymer having three or more nitrogen atoms (to be referred to as "nitrogen-containing compound (III)" hereinafter), amide group-containing compound, urea compound or nitrogen-containing heterocyclic compound.

Examples of the nitrogen-containing compound (I) include monoalkylamines such as n-hexylamine, n-heptylamine, n-octylamine, n-nonylamine, n-decylamine and cyclohexylamine; dialkylamines such as di-n-butylamine, di-n-pentylamine, di-n-hexylamine, di-n-heptylamine, di-n-octylamine, di-n-nonylamine, di-n-decylamine, methyl cyclohexylamine and dicyclohexylamine; trialkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, dimethyl cyclohexylamine, methyl dicyclohexylamine and tricyclohexylamine; and aromatic amines such as aniline, N-methylaniline, N,N-dimethylaniline, 2-methylaniline, 3-methylaniline, 4-methylaniline, 4-nitroaniline, diphenylamine, triphenylamine and 1-naphthylamine.

Examples of the nitrogen-containing compound (II) include ethylenediamine, N,N,N',N'-tetramethylethylenediamine, N,N,N',N'-tetrakis(2-hydroxypropyl)ethylenediamine, tetramethylenediamine, hexamethylenediamine, 4,4'-diaminodiphenylmethane, 4,4'-diaminodiphenylether, 4,4'-diaminobenzophenone, 4,4'-diaminodiphenylamine, 2,2-bis(4'-aminophenyl)propane, 2-(3'-aminophenyl)-2-(4'-aminophenyl)propane, 2-(4'-aminophenyl)-2-(3'-hydroxyphenyl)propane, 2-(4'-aminophenyl)-2-(4'-hydroxyphenyl)propane, 1,4-bis[1'-(4"-aminophenyl)-1'-methylethyl]benzene, 1,3-bis[1'-(4"-aminophenyl)-1'-methylethyl]benzene, bis(2-dimethylaminoethyl)ether and bis(2-diethylaminoethyl)ether.

Examples of the nitrogen-containing compound (III) include (co)polymers of polyethyleneimine, polyallylamine and N-2-dimethylaminoethyl acrylamide.

Examples of the above amide group-containing compound include formamide, N-methylforamide, N,N-dimethylformamide, acetamide, N-methylacetamide, N,N-dimethylacetamide, propionamide, benzamide, pyrrolidone and N-methylpyrrolidone.

Examples of the above urea compound include urea, methylurea, 1,1-dimethylurea, 1,3-dimethylurea, 1,1,3,3-tetramethylurea, 1,3-diphenylurea and tri-n-butylthiourea.

Examples of the above nitrogen-containing heterocyclic compound include imidazoles such as imidazole, benzimidazole, 4-methylimidazole, 4-methyl-2-phenylimiadzole and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, 2,2',6',2"-terpyridine, nicotine, nicotinic acid,: nicotinamide, quinoline, 8-oxyquinoline and acridine; pyrazine, pyrazole, pyridazine, quinoxaline, purine, pyrrolidine, piperidine, morpholine, 4-methylmorpholine, piperazine, 1,4-dimethylpiperazine and 1,4-diazabicyclo[2.2.2]octane.

Out of these nitrogen-containing compounds, the nitrogen-containing compounds (I), nitrogen-containing compounds (II) and nitrogen-containing heterocyclic compounds are preferred.

The above acid diffusion control agents may be used alone or in combination of two or more.

The amount of the acid diffusion control agent is preferably 15 parts or less by weight, more preferably 0.001 to 10 parts by weight, particularly preferably 0.005 to 5 parts by weight based on 100 parts by weight of the polymer (A). When the amount of the acid diffusion control agent is larger than 15 parts by weight, the sensitivity of the composition as a resist and the developability of an exposed portion tend to lower. When the amount of the acid diffusion control agent is smaller than 0.001 part by weight, the pattern shape and dimensional accuracy of the composition as a resist may lower according to process conditions.

The radiation sensitive resin composition of the present invention may comprise a surfactant which shows the function of improving the coatability and striation of the composition and the developability of the composition as a resist.

Examples of the surfactant include polyoxyethylene lauryl ether, polyoxyethylene stearyl ether, polyoxyethylene oleyl ether, polyoxyethylene n-octylphenol ether, polyoxyethylene n-nonylphenol ether, polyethylene glycol dilaurate and polyethylene glycol distearate. Commercially available products of the surfactant include F Top EF301, EF303 and EF352 (of Tokem Products Co., Ltd.), Megafax F171 and F173 (of Dainippon Ink and Chemicals, Inc.), Florade FC430 and FC431 (of Sumitomo 3M Limited), Asahi Guard AG710, Surflon S-382, SC101, SC102, SC103, SC104, SC105 and SC106 (of Asahi Glass Co., Ltd.), KP341 (of Shin-Etsu Chemical Co., Ltd.) and Polyflow No. 75 and No. 95 (of Kyoeisha Kagaku Co., Ltd.).

The above surfactants may be used alone or in combination of two or more. The amount of the surfactant is preferably 2 parts or less by weight based on 100 parts by weight of the polymer (A).

The radiation sensitive resin composition of the present invention may further comprise a sensitizer which shows the function of absorbing the energy of radiation and transmitting the energy to the acid generating agent (B) to increase the amount of an acid and has the effect of improving the apparent sensitivity of the resist.

Preferred examples of the sensitizer include benzophenones, Rose Bengales and anthracenes.

The amount of the sensitizer is preferably 50 parts or less by weight based on 100 parts by weight of the polymer (A).

The latent image of an exposed portion can be visualized and the influence of halation at the time of exposure can be alleviated by blending a dye and/or a pigment and adhesion to a substrate can be improved by blending an adhesive aid.

In addition to the above additives, a halation preventing agent such as 4-hydroxy-4'-methyl chalcone, shape improving agent, storage stabilizer, anti-foaming agent and other additives may also be blended.

The radiation sensitive resin composition of the present invention is prepared in the form of a solution by uniformly dissolving the composition in a solvent to ensure that the total solids content should become 1 to 50 wt %, preferably 5 to 40 wt % and filtering the resulting solution with a filter having an opening diameter of about 0.2 µm before use.

Examples of the solvent used to prepare the above composition solution include ethylene glycol monoalkyl ether acetates such as ethylene glycol monomethyl ether acetate, ethylene glycol monoethyl ether acetate, ethylene glycol mono-n-propyl ether acetate and ethylene glycol mono-n-butyl ether acetate; propylene glycol monoalkyl ethers such as propylene glycol monomethyl ether, propylene glycol monoethyl ether, propylene glycol mono-n-propyl ether and propylene glycol mono-n-butyl ether; propylene glycol dialkyl ethers such as propylene glycol dimethyl ether, propylene glycol diethyl ether, propylene glycol di-n-propyl ether and propylene glycol di-n-butyl ether; propylene glycol monoalkyl ether acetates such as propylene glycol monomethyl ether acetate, propylene glycol monoethyl ether acetate, propylene glycol mono-n-propyl ether acetate and propylene glycol mono-n-butyl ether acetate; lactates such as methyl lactate, ethyl lactate, n-propyl lactate and i-propyl lactate; aliphatic carboxylates such as n-amyl formate, i-amyl formate, ethyl acetate, n-propyl acetate, i-propyl acetate, n-butyl acetate, i-butyl acetate, n-amyl acetate, i-amyl acetate, i-propyl propionate, n-butyl propionate and i-butyl propionate; other esters such as ethyl hydroxyacetate, ethyl 2-hydroxy-2-methylpropionate, methyl 2-hydroxy-3-methylbutyrate, ethyl methoxyacetate, ethyl ethoxyacetate, methyl 3-mnethoxypropionate, ethyl 3-methoxypropionate, methyl 3-ethoxypropionate, ethyl 3-ethoxypropionate, 3-methylbutylacetate, 3-methyl-3-methoxybutylacetate, 3-methyl-3-methoxybutylpropionate, 3-methyl-3-methoxybutylbutyrate, methyl acetoacetate, ethyl acetoacetate, methyl pyruvate and ethyl pyruvate; aromatic hydrocarbons such as toluene and xylene; ketones such as methyl ethyl ketone, 2-pentanone, 2-hexanone, 2-heptanone, 3-heptanone, 4-heptanone and cyclohexanone; amides such as N-methylformamide, N,N-dimethylformamide, N-methylacetamide, N,N-dimethylacetamide and N-methylpyrrolidone; and lactones such as γ-butyrolactone.

These solvents may be used alone or in combination of two or more.

Formation of Resist Pattern

To form a resist pattern from the radiation sensitive resin composition of the present invention, the composition solution prepared as described above is applied to a substrate such as a silicon wafer or a wafer coated with aluminum by suitable coating means such as rotational coating, cast coating or roll coating to form a resist film which is then prebaked (to be abbreviated as PB hereinafter) at a temperature of 70 to 160° C. according to the circumstances and exposed through a predetermined mask pattern.

The radiation used for exposure is suitably selected from far ultraviolet radiation typically from an ArF excimer laser (wavelength of 193 nm) or KrF excimer laser (wavelength of 248 nm), charged corpuscular beams such as electron beams and X-radiation such as synchrotron radiation according to the type of the acid generating agent (B). Exposure conditions such as the amount of exposure are suitably selected according to the composition of the radiation sensitive resin composition and the types of additives.

To form a highly accurate fine pattern stably in the present invention, post-exposure baking (to be abbreviated as PEB hereinafter) is preferably carried out at a temperature of 70 to 160° C. for 30 seconds or more after exposure. When the temperature of PEB is lower than 70° C., differences in sensitivity according to the type of the substrate may become large.

Thereafter, the exposed resist film is developed with an alkali developer at preferably 10 to 50° C. for 10 to 200 seconds, more preferably at 15 to 30° C. for 15 to 100 seconds, particularly preferably at 20 to 25° C. for 15 to 90 seconds to form a predetermined resist pattern.

The above alkali developer is, for example, an alkaline aqueous solution prepared by dissolving at least one alkaline compound such as an alkali metal hydroxide, ammonia water, mono-, di- or tri-alkylamine, mono-, di- or tri-alkanolamine, heterocyclic amine, tetraalkylammonium hydroxide, choline, 1,8-diazabicyclo[5.4.0]-7-undecene or 1,5-diazabicyclo[4.3.0]-5-nonene to a concentration of preferably 1 to 10 wt %, more preferably 1 to 5 wt %, particularly preferably 1 to 3 wt %.

The above developer which is an alkaline aqueous solution may contain a water-soluble organic solvent such as methanol or ethanol and a surfactant in a suitable amount. After development with an alkali developer, the film is preferably rinsed in water and dried.

An organic or inorganic anti-reflection film may be formed on the substrate to. develop the maximum potential of the radiation sensitive resin composition before the formation of a resist pattern, and a protective film may also be formed on the resist film to prevent the influence of basic impurities contained in an environmental atmosphere, or these technologies may be combined together.

EXAMPLES

The following examples are provided for the purpose of further illustrating the present invention but are in no way to be taken as limiting.

Example 1

Figure 2:
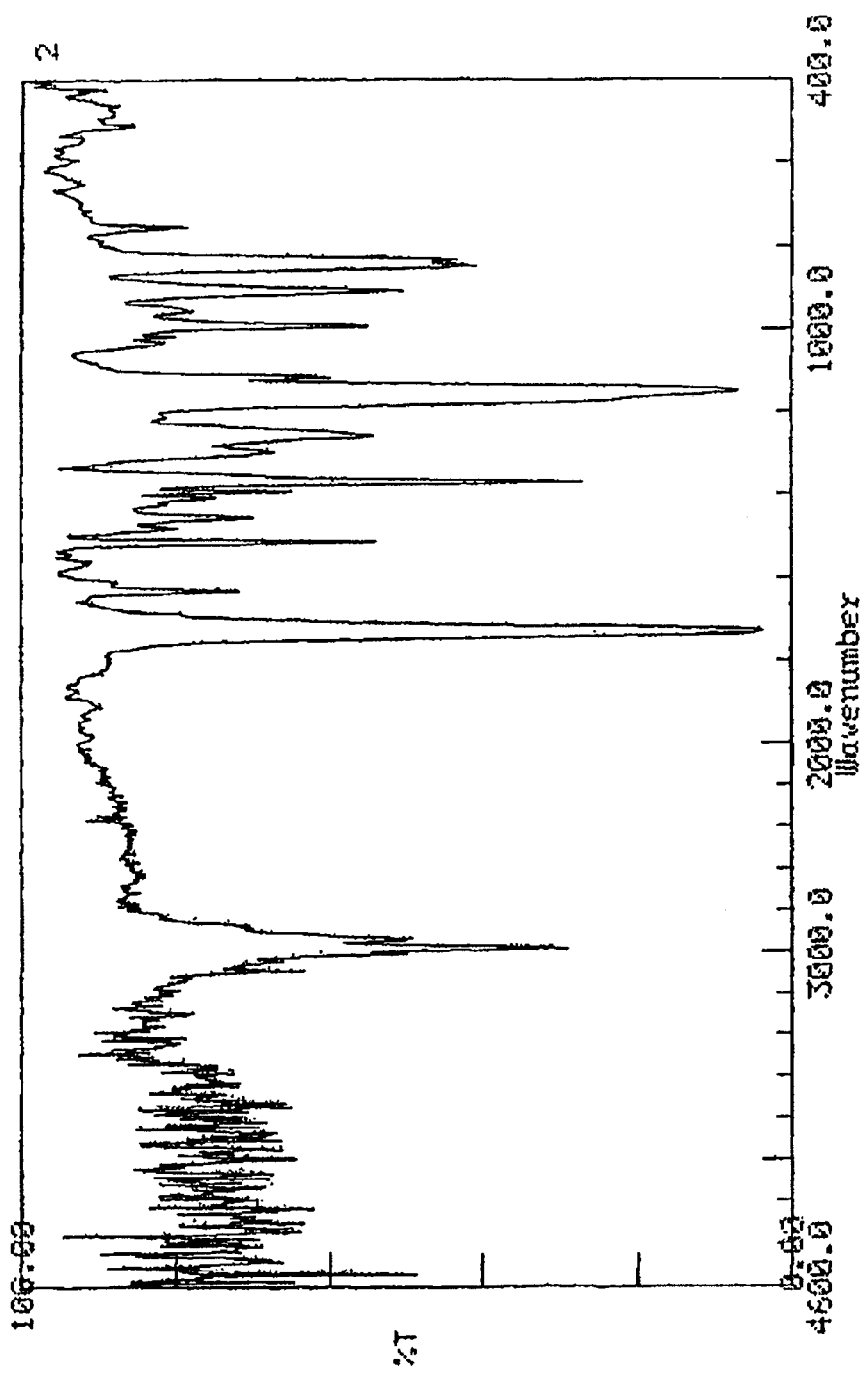
FIG. 2 is an infrared absorption spectrum diagram of the compound obtained in Example 1.

47 g (0.23 mol) of tri-n-butylphosphine and 90 ml of tetrahydrofuran (THF) were fed to a 1-liter three-necked flask and then 44.8 g (0.23 mol) of t-butyl bromoacetate was added dropwise to the solution under stirring at room temperature in a stream of nitrogen and stirred for 12 hours. Thereafter, the reactor was cooled with ice, 30 g (0.27 mol) of t-butoxy potassium dissolved in 100 ml of THF was added dropwise and stirred for 45 minutes, the reactor was returned to normal temperature, and 0.5 g of 2,4,6-tris(3', 5'-di-t-butyl-4'-hydroxybenzyl) methylstyrene was added. After 40 g (0.26 mol) of p-chloromesitylene was added dropwise and stirred at 40° C. for 12 hours, 140 g of a 10% aqueous solution of potassium carbonate was added and stirred at 40° C. for 8 hours to carry out hydrolysis. THF contained in the reaction solution was distilled off under reduced pressure and the reaction product was extracted with n-hexane, washed with saturated brine and purified by silica gel column chromatography to obtain 38 g of the achromatic transparent liquid compound (t-butyl 4-vinylphenylpropionate, molecular formula: $C_{15}H_{20}O_2$) of the present invention represented by the following formula. The yield was 71%. According to the elemental analysis (wt %), C: 77.32 (calculated value: 77.55) and H: 8.44 (calculated value: 8.68). FIG. 1 shows a nuclear magnetic resonance spectrum of this compound and FIG. 2 shows an infrared absorption spectrum of this compound.

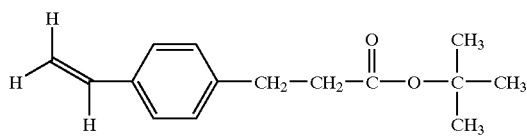

Example 2

(1) Synthesis of 4-vinylphenylpropionic Acid (Above Formula (5-1))

Figure 3:
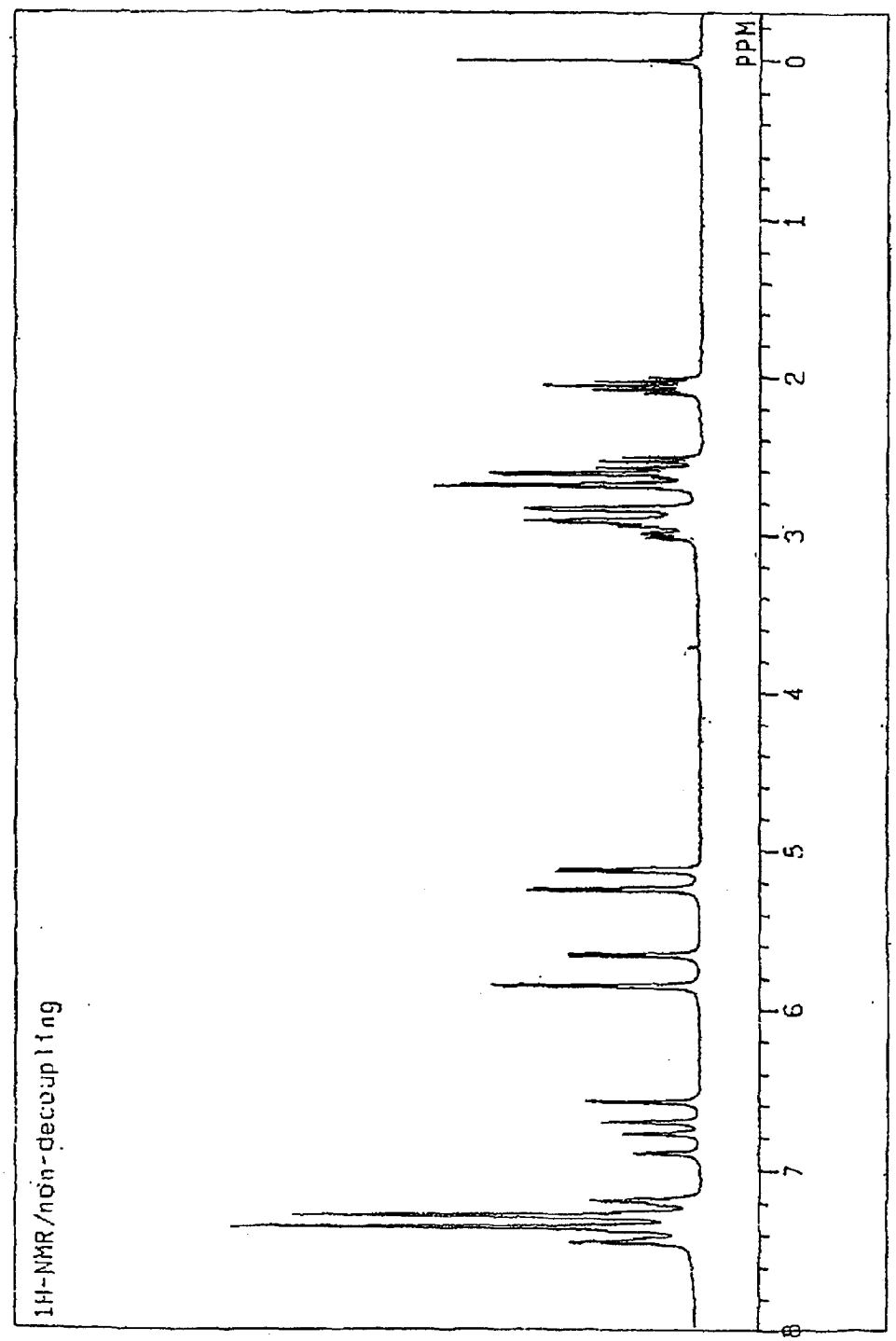
FIG. 3 is a nuclear magnetic resonance spectrum diagram of a compound obtained in (1) of Example 2.
Figure 4:
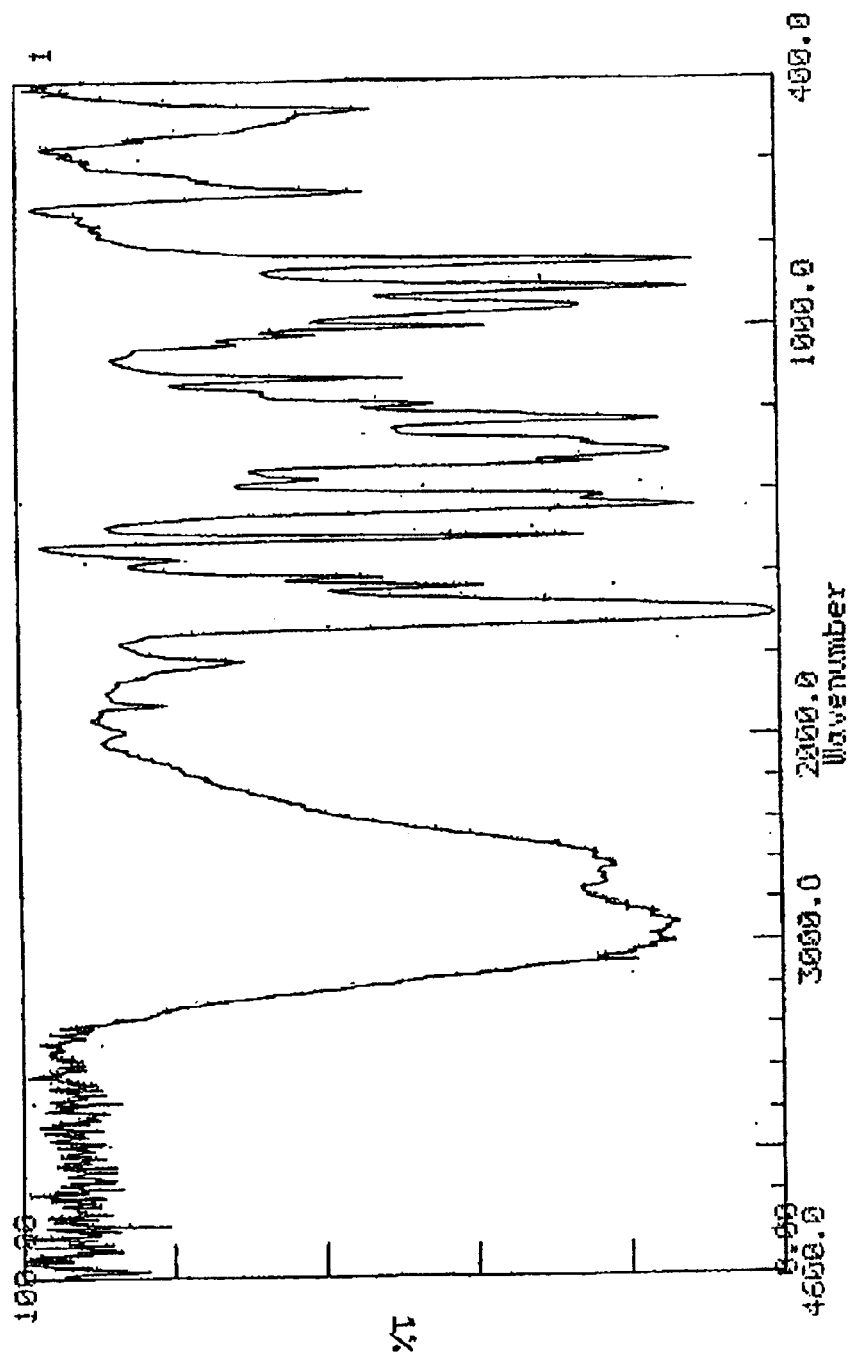
FIG. 4 is an infrared absorption spectrum diagram of the compound obtained in (1) of Example 2.

20 g (0.1 mol) of ethyl 4-vinylphenylpropionate was fed to a 1-liter three-necked flask, 100 ml of THF was added and well dissolved, and further 0.3 g of 2,4,6-tris(3',5'-di-t-butyl-4'-hydroxybenzyl)mesitylene was added. 100 ml of a 1.5 N aqueous solution of sodium hydroxide was added dropwise under stirring at room temperature and stirred at 50° C. for 1.5 hours. After THF was distilled off under reduced pressure and the reaction product was extracted with 100 ml of n-hexane twice, 15 ml of 37% concentrated hydrochloric acid was added dropwise under stirring to produce a white precipitate. The precipitate was separated by filtration, washed in cold water completely and vacuum dried at 50° C. for 12 hours to obtain 12 g of 4-vinylphenylpropionic acid ($C_{11}H12O_2$). The yield was 68%. According to elemental analysis (wt %), C: 74.76 (calculated value: 74.98) and H: 6.91 (calculated value: 6.86). FIG. 3 shows a nuclear magnetic resonance spectrum of this compound and FIG. 4 shows an infrared absorption spectrum of this compound.

Figure 5:
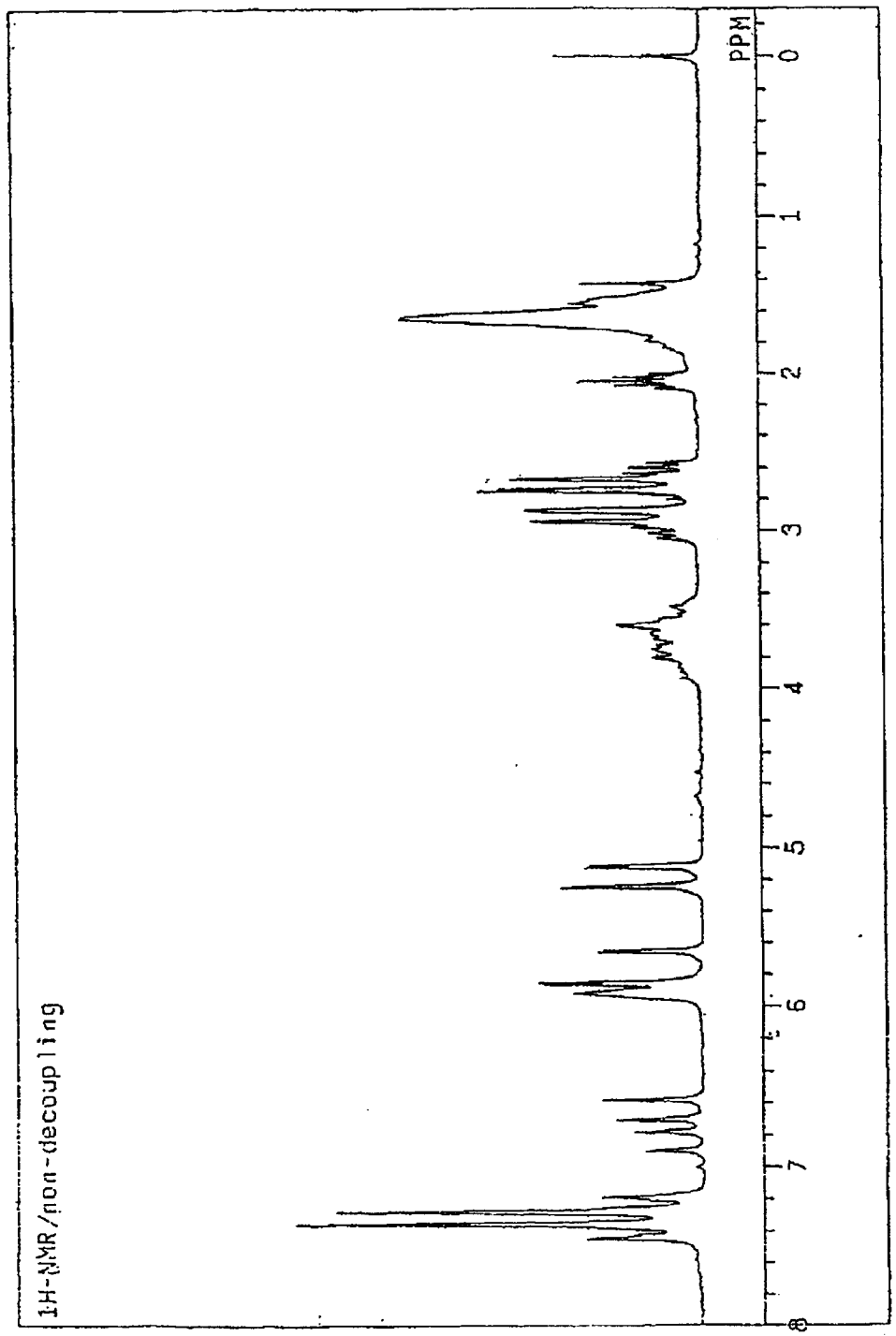
FIG. 5 is a nuclear magnetic resonance spectrum diagram of a compound obtained in (2) of Example 2.
Figure 6:
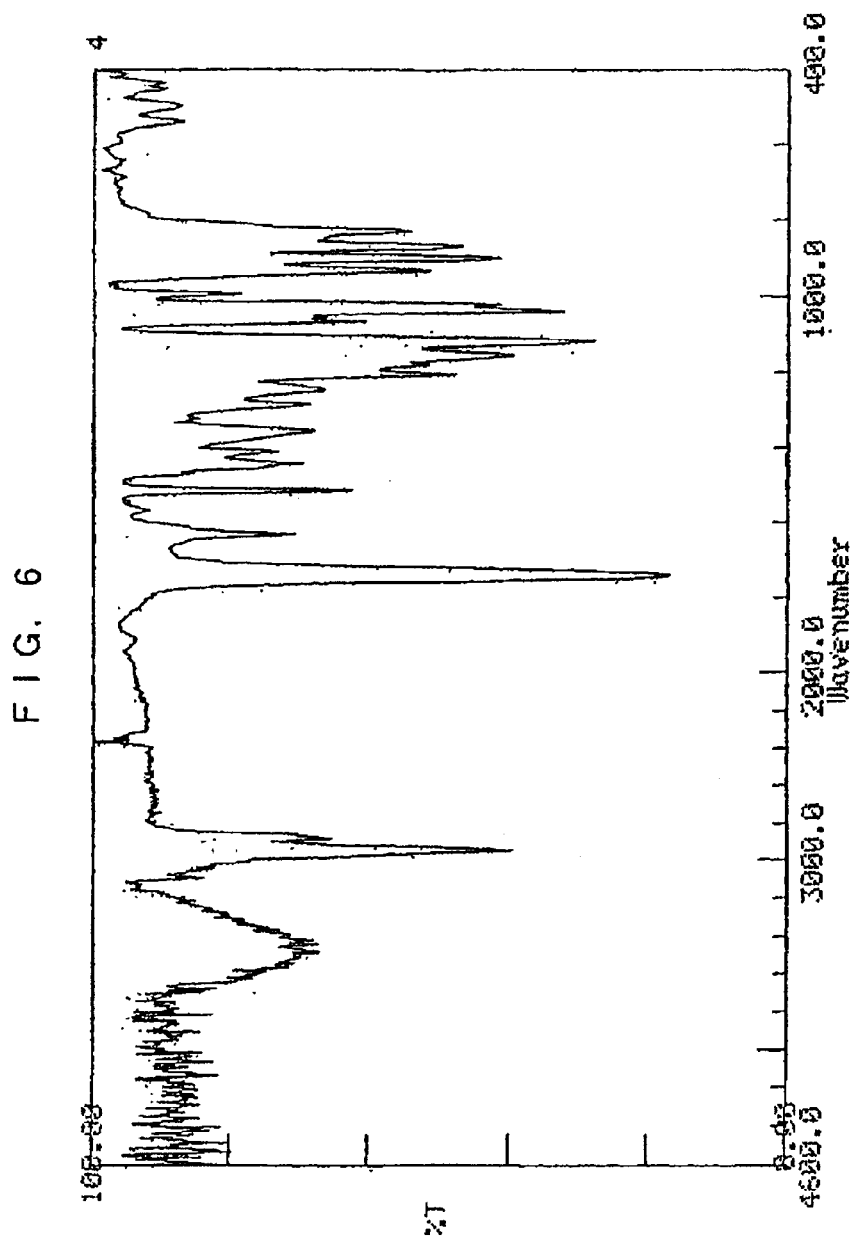
FIG. 6 is an infrared absorption spectrum diagram of the compound obtained in (2) of Example 2.

(2) Synthesis of 4-vinylphenylpropionic Acid-2'-tetrahydropyranyl 17.6 g (0.1 mol) of 4-vinylphenylpropionic acid obtained in (1), 0.5 g of 2,4,6-tris(3',5'-di-t-butyl-4'-hydroxybenzyl) mesitylene and 20 ml of 3,4-dihydro-2H-pyran were fed to a 200 ml three-necked flask equipped with a reflex condenser and stirred at 60° C. for 10 hours. Thereafter, the reaction solution was returned to normal temperature and purified by silica gel column chromatography to obtain 14 g of the compound (4-vinylphenylpropinic acid-2'-tetrahydropyranyl, molecular formula: $C_{16}H_{20}O_3$) of the present invention represented by the following formula. The yield was 54%. According to elemental analysis (wt %), C: 73.73 (calculated value: 73.82) and H: 7.65 (calculated value: 7.74). FIG. 5 shows a nuclear magnetic resonance spectrum of this compound and FIG. 6 shows an infrared absorption spectrum of this compound.

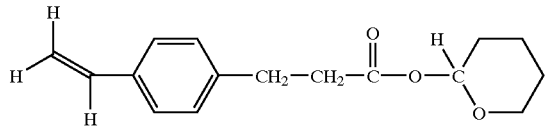

Example 3

Figure 7:
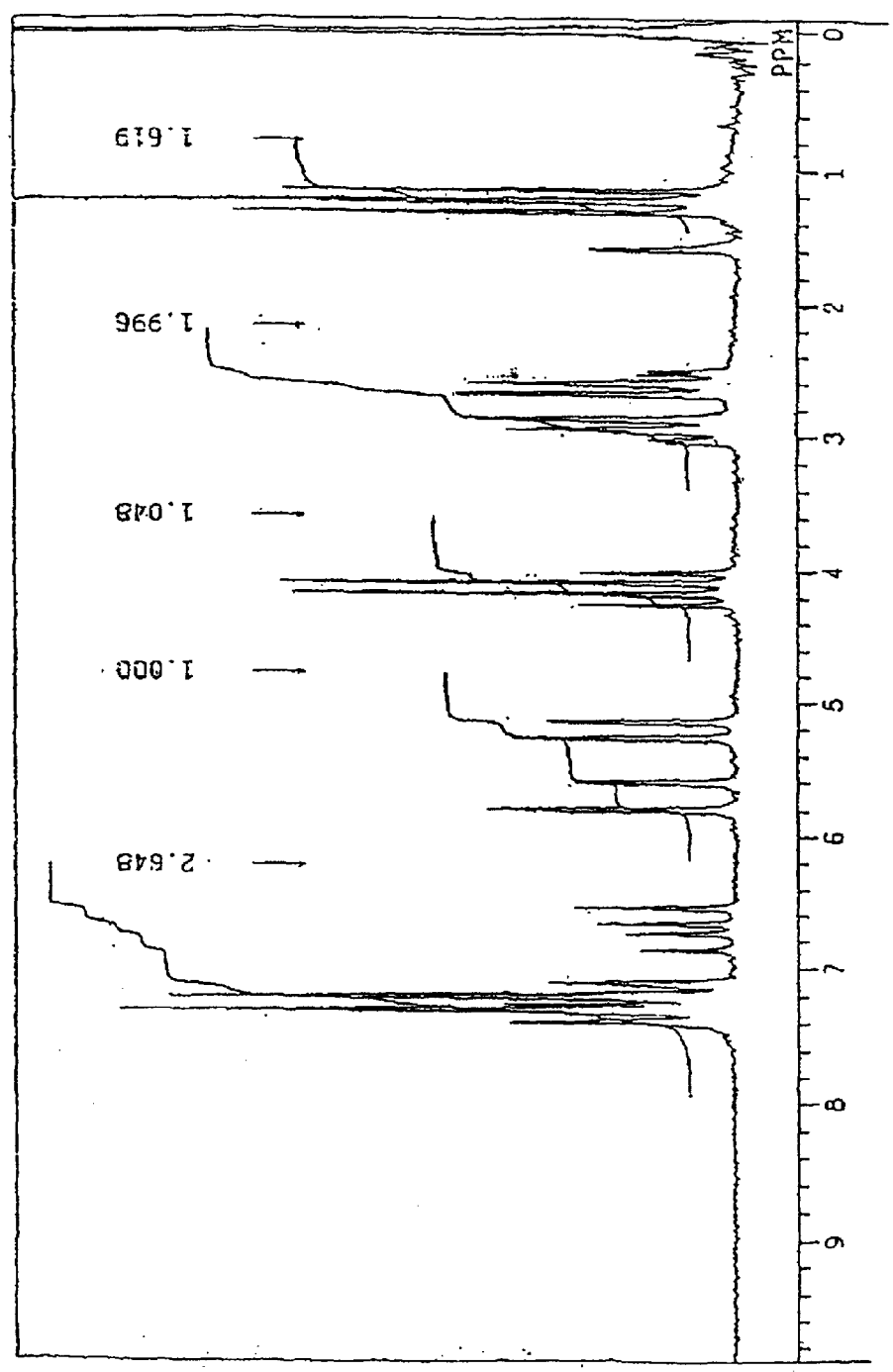
FIG. 7 is a nuclear magnetic resonance spectrum diagram of a compound obtained in Example 3.
Figure 8:
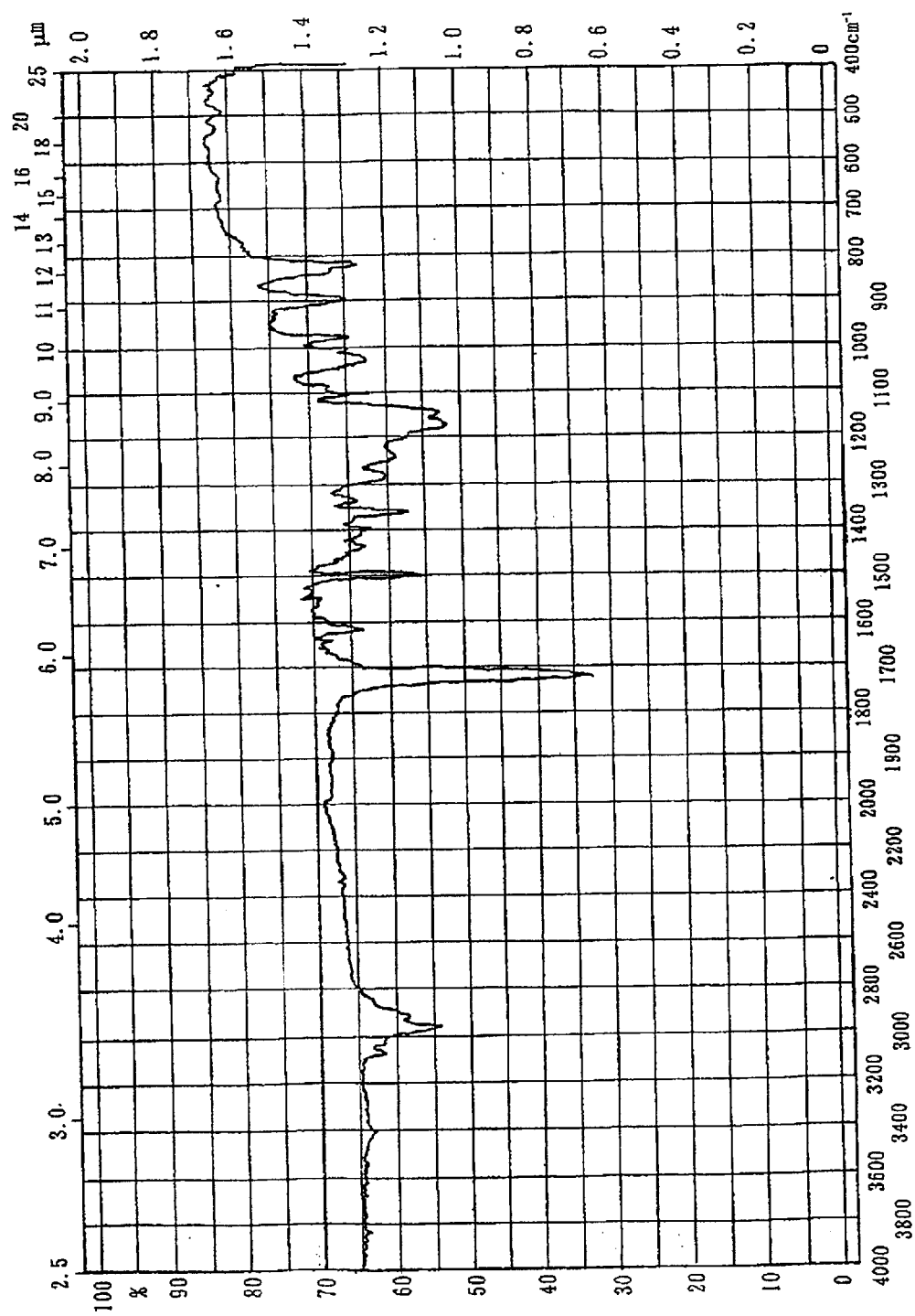
FIG. 8 is an infrared absorption spectrum diagram of the compound obtained in Example 3.

34 g of a compound represented by the following formula (ethyl 4-vinylphenylpropionate, molecular formula: $C_{13}H_{16}O_2$) was obtained in the same manner as in Example 1 except that 38 g (0.23 mol) of ethyl bromoacetate was used. The yield was 73%. According to elemental analysis (wt %), C: 76.78 (calculated value: 76.44) and H: 7.84 (calculated value: 7.90). FIG. 7 shows a nuclear magnetic resonance spectrum of this compound and FIG. 8 shows an infrared absorption spectrum of this compound.

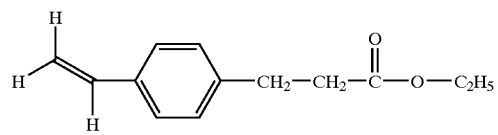

Example 4

Figure 9:
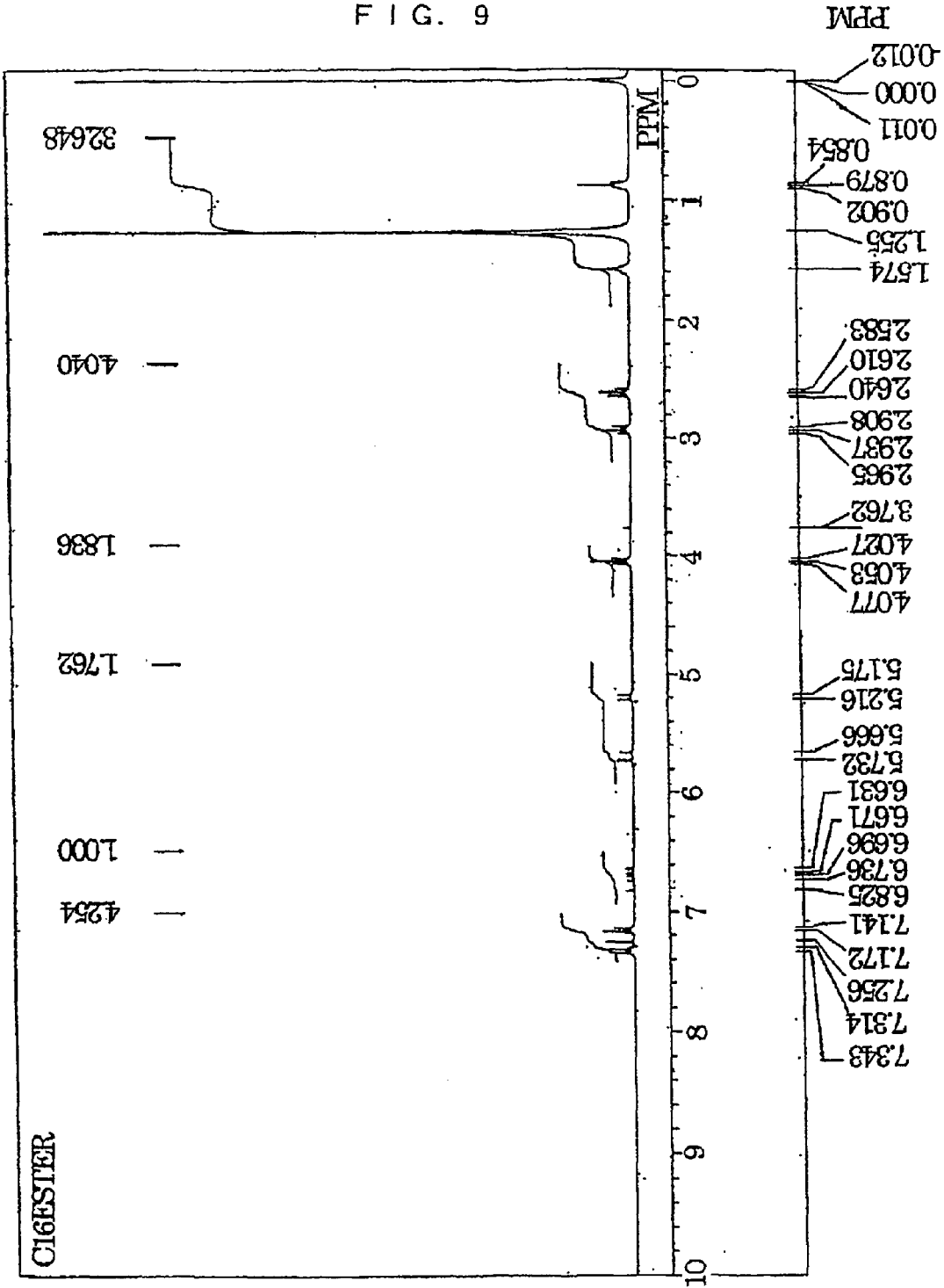
FIG. 9 is a nuclear magnetic resonance spectrum diagram of a compound obtained in Example 4.
Figure 10:
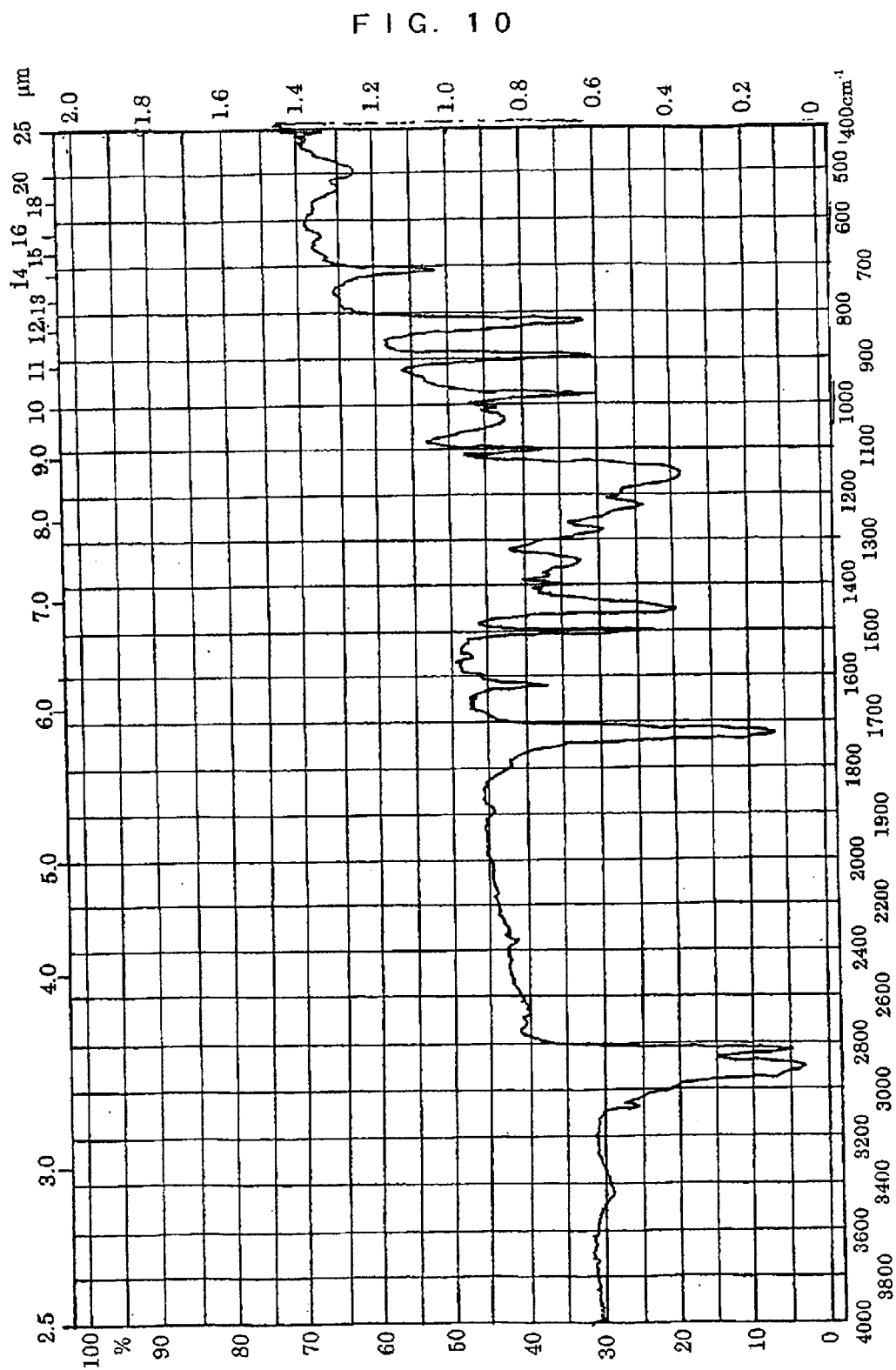
FIG. 10 is an infrared absorption spectrum diagram of the compound obtained in Example 4.

53 g of a compound represented by the following formula (1-hexadecanyl 4-vinylphenylpropionate, molecular formula: $C_{27}H_{44}O_2$) was obtained in the same manner as in Example 1 except that 84 g (0.23 mol) of 1-hexadecanyl bromoacetate was used. The yield was 57%. (1-hexadecanyl bromoacetate used in this synthesis was synthesized by an ordinary ester synthesis method using bromoacetyl bromide and 1-hexadecanol) According to elemental analysis (wt %), C: 80.78 (calculated value: 80.94) and H:11.12 (calculated value: 11.07). FIG. 9 shows a nuclear magnetic resonance spectrum of this compound and FIG. 10 shows an infrared absorption spectrum of this compound.

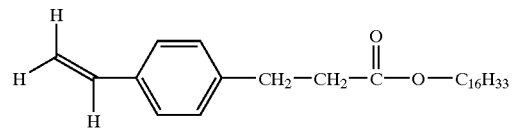

Example 5

15 g of t-butyl 4-vinylphenylpropionate obtained in Example 1, 15 g of 1-acryloyloxy-3-hydroxyadamantane, 20 g of p-acetoxystyrene, 0.34 g of t-dodecylmercaptan, 1.68 g of azobisisobutyronitrile and 50 g of propylene glycol monomethyl ether were added to a 300 ml Kjeldahl-shaped flask whose inside had been substituted by nitrogen to carry out polymerization in a stream of nitrogen at 75° C. for 7 hours. After the end of polymerization, the reaction solution was cooled and poured into a large amount of methanol, the precipitated polymer was separated by decantation, and 15 g of triethylamine was added to carry out a reaction in order to hydrolyze the acetoxy group contained in the p-acetoxystyrene unit.

The obtained polymer was a copolymer of t-butyl 4-vinylphenylpropionate/1-acryloyloxy-3-hydroxyadamantane/p-hydroxystyrene (weight ratio of 30/30/40), and had an Mw of 14,000. The yield was 70%. This polymer was designated as polymer (A-1).

Example 6

15 g of t-butyl 4-vinylphenylpropionate obtained in Example 1, 15 g of 1-acryloyloxy-3-hydroxyadamantane, 20 g of 4-vinylphenylpropionic acid obtained in Example 2(1), 0.32 g of t-dodecylmercaptan, 1.61 g of azobisisobutyronitrile and 50 g of propylene glycol monomethyl ether were added to a 300 ml Kjeldahl-shaped flask whose inside had been substituted by nitrogen to carry out polymerization in a stream of nitrogen at 75° C. for 7 hours. After the end of polymerization, the reaction solution was cooled and poured into a large amount of methanol, and the precipitated polymer was separated by decantation.

The obtained polymer was a copolymer of t-butyl 4-vinylphenylpropionate/1-acryloyloxy-3-hydroxyadamantane/4-vinylphenylpropionic acid (weight ratio of 30/30/40) and had an Mw of 14,000. The yield was78%. Thispolymerwasdesignatedaspolymer(A-2).

Example 7

20 g of t-butyl 4-vinylphenylpropionate obtained in Example 1, 10 g of 3-acryloyloxymethyl-8-hydroxytetracyclododecane, 20 g of p-acetoxystyrene, 0.32 g of t-dodecylmercaptan, 1.62 g of azobisisobutyronitrile and 50 g of propylene glycol monomethyl ether were added to a 300 ml Kjeldahl-shaped flask whose inside had been substituted by nitrogen to carry out polymerization in a stream of nitrogen at 75° C. for 7 hours. After the end of polymerization, the reaction solution was cooled and poured into a large amount of methanol, the precipitated polymer was separated by decantation, and 15 g of triethylamine was added to carry out a reaction in order to hydrolyze an acetoxy group contained in the p-acetoxystyrene unit.

The obtained polymer was a copolymer of t-butyl 4-vinylphenylpropionate/3-acryloyloxymethyl-8-hydroxytetracyclododecane/p-hydroxystyrene (weight ratio of 40/20/40) and had an Mw of 14,000. The yield was 68%. This polymer was designated as polymer (A-3).

Example 8

15 g of 2'-tetrahydropyranyl 4-vinylphenylpropionate obtained in Example 2(2), 15 g of 1-acryloyloxy-3-hydroxyadamantane, 20 g of p-acetoxystyrene, 0.33 g of t-dodecylmercaptan, 1.63 g of azobisisobutyronitrile and 50 g of propylene glycol monomethyl ether were added to a 300 ml Kjeldahl-shaped flask whose inside had been substituted by nitrogen to carry out polymerization in a stream of nitrogen at 75° C. for 7 hours. After the end of polymerization, the reaction solution was cooled and poured into a large amount of methanol, the precipitated polymer was separated by decantation, and 15 g of triethylamine was added to carry out a reaction in order to hydrolyze an acetoxy group contained in the p-acetoxystyrene unit.

The obtained polymer was a copolymer of 2'-tetrahydropyranyl 4-vinylphenylpropionate/1-acryloyloxy-3-hydroxyadamantane/p-hydroxystyrene (weight ratio of 30/30/40) and had an Mw of 14,000. The yield was 72%. This polymer was designated as polymer (A-4).

Example 9

15 g of 2'-tetrahydropyranyl 4-vinylphenylpropionate obtained in Example 2(2), 15 g of 1-acryloyloxy-3-hydroxyadamantane, 20 g of 4-vinylphenylpropionic acid obtained in Example 2(1), 0.31 g of t-dodecylmercaptan, 1.57 g of azobisisobutyronitrile and 50 g of propylene glycol monomethyl ether were added to a 300 ml Kjeldahl-shaped flask whose inside had been substituted by nitrogen to carry out polymerization in a stream of nitrogen at 75° C. for 7 hours. After the end of polymerization, the reaction solution was cooled and poured into a large amount of methanol, and the precipitated polymer was separated by decantation.

The obtained polymer was a copolymer of 2'-tetrahydropyranyl 4-vinylphenylpropionate/1-acryloyloxy-3-hydroxyadamantane/4-vinylphenylpropionic acid (weight ratio of 30/30/40) and had an Mw of 14,000. The yield was80%. Thispolymerwasdesignatedaspolymer (A-5).

Example 10

20 g of 2'-tetrahydropyranyl 4-vinylphenylpropionate obtained in Example 2(2), 10 g of 3-acryloyloxymethyl-8-hydroxytetracyclododecane, 20 g of p-acetoxystyrene, 0.31 g of t-dodecylmercaptan, 1.56 g of azobisisobutyronitrile and 50 g of propylene glycol monomethyl ether were added to a 300 ml Kjeldahl-shaped flask whose inside had been substituted by nitrogen to carry out polymerization in a stream of nitrogen at 75° C. for 7 hours. After the end of polymerization, the reaction solution was cooled and poured into a large amount of methanol, the precipitated polymer was separated by decantation, and 15 g of triethylamine was added to carry out a reaction in order to hydrolyze an acetoxy group contained in the p-acetoxystyrene unit.

The obtained polymer was a copolymer of 2'-tetrahydropyranyl 4-vinylphenylpropionate/3-acryloyloxymethyl-8-hydroxytetracyclododecane/p-hydroxystyrene (weight ratio of 40/20/40) and had an Mw of 14,000. The yield was 67%. This polymer was designated as polymer (A-6).

Example 11

12.5 g of t-butyl 4-vinylphenylpropionate obtained in Example 1, 12.5 g of 1-acryloyloxy-3-hydroxyadamantane, 22.5 g of 4-vinylphenylpropionic acid obtained in Example 2(1), 2.5 g of 2,5-dimethyl-2,5.-hexanediol diacrylate, 0.97 g of t-dodecylmercaptan, 1.62 g of azobisisobutyronitrile and 60 g of propylene glycol monbmethyl ether were added to a 300 ml Kjeldahl-shaped flask whose inside had been substituted by nitrogen to carry out polymerization in a stream of nitrogen at 75° C. for 7 hours. After the end of polymerization, the reaction solution was cooled and poured into a large amount of methanol, and the precipitated polymer was separated by decantation.

The obtained polymer was a copolymer of t-butyl 4-vinylphenylpropionate/1-acryloyloxy-3-hydroxyadamantane/4-vinylphenylpropinic acid/2,5-dimethyl-2,5-hexanediol diacrylate (weight ratio of 25/25/45/5) and had an Mw of 30,000. The yield was 81%. This polymer was designated as polymer (A-7).

Example 12

12.5 g of t-butyl 4-vinylphenylpropionate obtained in Example 1, 12.5 g of 1-acryloyloxy-3-hydroxyadamantane, 22.5 g of 4-vinylphenylpropionic acid obtained in Example 2(1), 2.5 g of tricyclodecanedimethanol diacrylate, 0.97 g of t-dodecylmercaptan, 1.61 g of azobisisobutyronitrile and 60 g of propylene glycol monomethyl ether were added to a 300 ml Kjeldahl-shaped flask whose inside had been substituted by nitrogen to carry out polymerization in a stream of nitrogen at 75° C. for 7 hours. After the end of polymerization, the reaction solution was cooled and poured into a large amount of methanol, and the precipitated polymer was separated by decantation.

The obtained polymer was a copolymer of t-butyl 4-vinylphenylpropionate/1-acryloyloxy-3-hydroxyadamantane/4-vinylphenylpropinic acid/tricyclodecanedimethanol diacrylate (weight ratio of 25/25/45/5) and had an Mw of 30,000. The yield was 78%. This polymer was designated as polymer (A-8).

Examples 13 to 22 and Comparative Example 1

Components shown in Table 1 (parts are based on weight) were mixed together to prepare uniform solutions which were then filtered with a Teflon membrane filter having an opening diameter of 0.2 μm to prepare composition solutions.

Thereafter, each of the above composition solutions was applied to a silicone wafer by rotational coating and PB was carried at a temperature shown in Table 2 for a time shown in Table 2 to form a 0.5 μm-thick resist film. This resist film was then exposed to light from a KrF excimer laser (wavelength of 248 nm) through a mask pattern using the KrF excimer laser stepper (trade name: NSR-2205 EX12A, numerical aperture: 0.55) of Nikon Corporation by changing the amount of exposure. In some Examples, a simple electron beam direct drawing device (acceleration voltage of 50 KeV) was used in place of the KrF excimer laser to expose the resist film to electron beams through the mask pattern by changing the amount of exposure. After exposure, PEB was carried out at a temperature shown in Table 2 for a time shown in Table 2. Thereafter, the resist film was developed with an aqueous solution of tetramethylammonium hydroxide, rinsed in water for 30 seconds and dried to form a resist pattern.

The evaluation results of Examples and Comparative Examples are shown in Table 3.

The measurement of Mw and the evaluation of each resist were carried out as follows.

Mw

GPC columns (2×G2000HXL, 1×G3000HXL, 1×G4000HXL) manufactured by Toso Co., Ltd. are used to measure Mw by gel permeation chromatography (GPC) using monodisperse polystyrene as the standard under the following analytical conditions.

flow rate: 1.0 ml/minute
eluting solvent: tetrahydrofuran
column temperature: 40° C.

Sensitivity

The amount of exposure for forming a line-and-space pattern (1L1S) having a design line width of 0.22 μm to a line/space width ratio of 1:1 is taken as the optimum amount of exposure and sensitivity is evaluated based on this optimum amount of exposure.

Resolution

The minimum size of a resist pattern which is exposed to the optimum amount of light and resolved when a line-and-space pattern (1L1S) having a design line width of 0.22 μm is formed is taken as resolution.

Radiation Transmission

The transmission at a wavelength of 248 nm of a resist film formed by applying a composition solution to a circular quartz plate by spin coating and PB is measured by ultraviolet absorptiometry. The thickness of the resist film is measured with stylars based surf ace profiler film thickness measuring instrument and a transmission when the film thickness is 50 μm is calculated from the measured transmission and taken as radiation transmission.

PED Stability

A sample which is exposed to the optimum amount of light when PEB is carried right after exposure and developed is placed in a chamber in which the concentration of ammonia in the atmosphere is controlled to 5 ppb for 2 hours, PEB is carried and the sample is developed to form a line-and-space pattern (1L1S) having a design line width of 0.22 μm. The line width on the top of the pattern (Ltop) is measured by a scanning electron microscope and evaluated based on the following criteria.

| | |
|---|---|
| 0.22 × 0.85 < Ltop < 0.22 × 1.1: | satisfactory |
| 0.22 × 0.85 ≧ Ltop: | thin |
| 0.22 × 1.1 ≦ Ltop: | thick |

Components other than the polymers (A-1) to (A-7) used in Examples and Comparative Examples are as follows Other Polymer a-1: copolymer of p-hydroxystyrene/styrene/t-butyl acrylate (weight ratio of 60/20/20, Mw=14,000)

Acid Generating Agent (B)

B-1: triphenylsulfonium trifluoromethanesulfonate

B-2: N-(trifluoromethylsulfonyloxy)bicyclo[2.2.1]hept-5-ene-2,3-dicarboxyimide

B-3: bis(4-t-butylphenyl)iodonium 10-camphorsulfonate

B-4: bis(4-t-butylphenyl )iodonium nonafluoro-n-butanesulfonate

B-5: bis(1,4-dioxaspiro[4.5]decane-7-sulfonyl)diazomethane

Acid Diffusion Control Agent

C-1: N,N,N',N'-tetrakis(2-hydroxypropyl)ethylenediamine

C-2: 2-phenylbenzimidazole

C-3: tri-n-octylamine

C-4: 2,2',6',2"-terpyridlne

C-5: 4-phenylpyridine

Solvent

D-1: ethyl lactate

D-2: ethyl 3-ethoxypropionate

D-3: propylene glycol monomethyl ether acetate

D-4: 2-heptanone

TABLE 1

| | polymer (parts) | (B) acid generating agent (parts) | acid diffusion control agent (parts) | solvent (parts) |
|---|---|---|---|---|
| Ex.13 | A-1(100) | B-3(2.2) B-4(2.4) | C-1(0.2) | D-1(400) D-2(150) |
| Ex.14 | A-2(100) | B-3(2.2) B-4(2.4) | C-1(0.2) | D-1(400) D-3(150) |
| Ex.15 | A-2(100) | B-2(10.0) | C-2(0.1) | D-1(400) D-3(150) |
| Ex.16 | A-3(100) | B-3(2.2) B-4(2.4) | C-1(0.2) C-5(0.05) | D-1(400) D-2(150) |
| Ex.17 | A-4(100) | B-5(6.0) | C-3(0.1) | D-1(400) D-4(150) |
| Ex.18 | A-5(100) | B-5(6.0) | C-1(0.2) | D-1(400) D-2(150) |
| Ex.19 | A-5(100) | B-1(10.0) | C-3(0.1) | D-1(400) D-2(150) |
| Ex.20 | A-6(100) | B-5(6.0) | C-2(0.1) | D-1(400) D-3(150) |

TABLE 1-continued

| | polymer (parts) | (B) acid generating agent (parts) | acid diffusion control agent (parts) | solvent (parts) |
|---|---|---|---|---|
| Ex.21 | A-7(100) | B-3(2.2) B-4(2.4) | C-1(0.2) | D-1(400) D-4(150) |
| Ex.22 | A-8(100) | B-2(10.0) B-3(2.0) | C-4(0.1) | D-1(400) D-3(150) |
| C.Ex.1 | a-1(100) | B-3(2.2) B-4(2.4) | C-1(0.2) | D-1(400) D-2(150) |

Ex.: Example
C.Ex.: Comparative Example

TABLE 2

| | PB temperature (°C.) | PB time (sec) | Light source | PB temperature (°C.) | PB time (sec) |
|---|---|---|---|---|---|
| Ex.13 | 140 | 90 | KrF excimer laser | 140 | 90 |
| Ex.14 | 130 | 60 | KrF excimer laser | 130 | 90 |
| Ex.15 | 130 | 90 | KrF excimer laser | 110 | 60 |
| Ex.16 | 130 | 90 | KrF excimer laser | 140 | 90 |
| Ex.17 | 110 | 60 | KrF excimer laser | 100 | 90 |
| Ex.18 | 100 | 60 | KrF excimer laser | 100 | 90 |
| Ex.19 | 110 | 90 | Electron beam | 115 | 90 |
| Ex.20 | 90 | 90 | KrF excimer laser | 110 | 90 |
| Ex.21 | 140 | 90 | KrF excimer laser | 140 | 90 |
| Ex.22 | 130 | 90 | KrF excimer laser | 110 | 90 |
| C.Ex.1 | 140 | 90 | KrF excimer laser | 140 | 90 |

Ex.: Example
C.Ex.: Comparative Example

TABLE 3

| | sensitivity | resolution ($\mu$m) | radiation transmission (%) | PEB stability |
|---|---|---|---|---|
| Ex.13 | $2.2 \times 10^2$ J/m$^2$ | 0.20 | 80 | satisfactory |
| Ex.14 | $2.8 \times 10^2$ J/m$^2$ | 0.18 | 81 | satisfactory |
| Ex.15 | $3.0 \times 10^2$ J/m$^2$ | 0.20 | 85 | satisfactory |
| Ex.16 | $3.2 \times 10^2$ J/m$^2$ | 0.18 | 82 | satisfactory |
| Ex.17 | $2.5 \times 10^2$ J/m$^2$ | 0.18 | 86 | satisfactory |
| Ex.18 | $3.3 \times 10^2$ J/m$^2$ | 0.18 | 87 | satisfactory |
| Ex.19 | $7 \times 10^{-2}$ C/m$^2$ | 0.18 | 75 | satisfactory |
| Ex.20 | $2.7 \times 10^2$ J/m$^2$ | 0.18 | 88 | satisfactory |
| Ex.21 | $3.0 \times 10^2$ J/m$^2$ | 0.18 | 83 | satisfactory |
| Ex.22 | $3.1 \times 10^2$ J/m$^2$ | 0.18 | 81 | satisfactory |
| C.Ex.1 | $3.6 \times 10^2$ J/m$^2$ | 0.22 | 65 | thick |

Ex.: Example
C.Ex.: Comparative Example

Effect of the Invention

As described above, according to the present invention, novel vinylphenylpropionic acid derivatives can be obtained and a suitable substituent can be easily introduced into them. These vinylphenylpropionic acid derivatives have polymerization activity and polymers having physical properties suitable for application purpose can be obtained from vinylphenylpropionic acid derivatives having a suitable substituent. There is also provided a method of synthesizing these novel vinylphenylpropionic acid derivatives easily.

Particularly, a polymer containing a recurring unit represented by the above formula (1') as an essential unit has extremely low absorption of radiation and is very useful as a resin component of a radiation sensitive resin composition suitable for use as a chemically amplified resist. The radiation sensitive resin composition of the present invention containing this polymer can reduce the difference of effective exposure amount between an upper portion and a lower portion of a resist film, can ensure the rectangularity of even a fine pattern, has high sensitivity (small amount of exposure energy) to radiation such as far ultraviolet radiation typically from a KrF excimer laser or ArF excimer laser, charged corpuscular beams such as electron beams or X-radiation such as synchrotron radiation, is free from a change in the line width of a pattern formed therefrom or the T-shaped deformation of the pattern caused by fluctuations in PED and has excellent resolution. Therefore, the radiation sensitive resin composition of the present invention can be extremely advantageously used as a chemically amplified resist for the production of semiconductor devices whose design rule is expected to be much smaller in the future.

What is claimed is:

1. Vinylphenylpropionic acid derivatives represented by the following formula (1):

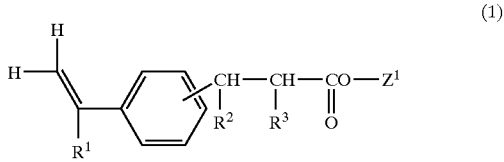

(1)

wherein $R^1$ is a hydrogen atom or a methyl group, $R^2$ is a hydrogen atom, an alkyl group having 1 to 8 carbon atoms which may be substituted or a phenyl group which may be substituted, $R^3$ is a hydrogen atom or a phenyl group which may be substituted and $Z^1$ is a group represented by the following formula (2):

(2)

wherein $R^4$ and $R^5$ may be the same or different and each is a hydrogen atom, an alkyl group having 1 to 8 carbon atoms which may be substituted or a phenyl group which may be substituted, and $R^6$ is an alkyl group having 1 to 8 carbon atoms which may be substituted or a phenyl group which may be substituted, or any two of $R^4$, $R^5$ and $R^6$ may be bonded together with a carbon atom bonded thereto to form a cyclic aliphatic group, or a group represented by the following formula (3):

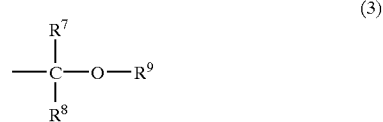

(3)

wherein $R^7$ and $R^8$ may be the same or different and each a hydrogen atom, an alkyl group having 1 to 8 carbon atoms which may be substituted or a phenyl group which may be substituted, $R^9$ is an alkyl group having 1 to 8 carbon atoms which may be substituted or a phenyl group which may be substituted, or any two of $R^7$, $R^8$ and $R^9$ may be bonded together with a carbon atom bonded thereto to form a cyclic aliphatic group, with proviso that the group represented by

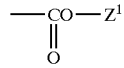

is an acid dissociable group which generates a carboxyl group (—COOH) in the presence of an acid.

2. A process for producing vinylphenylpropionic acid derivatives of claim 1, comprising the steps of:

(i) reacting an acetate represented by the following formula (4-1):

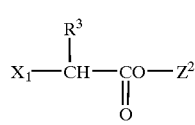

(4-1)

wherein $Z^2$ is a group represented by the following formula (2'):

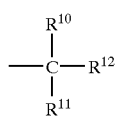

(2')

wherein $R^{10}$ and $R^{11}$ may be the same or different and each is a hydrogen atom, an alkyl group having 1 to 8 carbon atoms which may be substituted or a phenyl group which may be substituted, and $R^{12}$ is an alkyl group having 1 to 8 carbon atoms which may be substituted or a phenyl group which may be substituted, or any two of $R^{10}$, $R^{11}$ and $R^{12}$ may be bonded together with a carbon atom bonded thereto to form a cyclic aliphatic group, or a group represented by formula (3), and $X_1$ is an eliminating group, with a trialkylphosphine represented by the following formula (4-2):

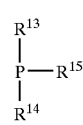

(4-2)

wherein $R^{13}$, $R^{14}$, and $R^{15}$ may be the same or different and each an alkyl group having 1 to 8 carbon atoms which may be substituted, to form a first quaternary phosphonium salt represented by the following formula (4-3):

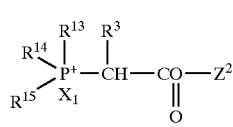

(4-3)

(ii) reacting the formed first quaternary phosphonium salt with a base to form a phosphorus ylide represented by the following formula (4-4):

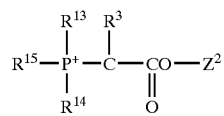

(4-4)

(iii) reacting the formed phosphorus ylide with a styrene derivative represented by the following formula (4-5):

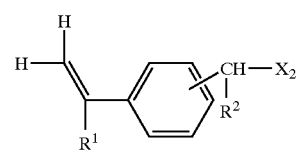

(4-5)

wherein $X_2$ is an eliminating group, to form a second quaternary phosphonium salt represented by the following formula (4-6):

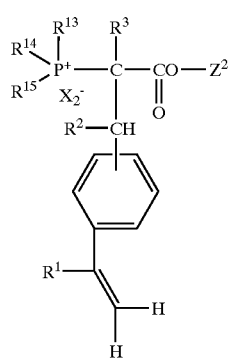

(4-6)

and (iv) hydrolyzing the formed quaternary phosphonium salt.

3. A polymer which comprises a recurring unit represented by the following formula (1'):

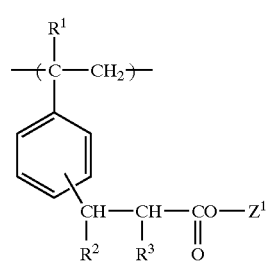

(1')

wherein $R^1$, $R^2$, $R^3$ and $Z^1$ are as defined in the above formula (1) of claim 1, and which has a weight average molecular weight in terms of polystyrene measured by gel permeation chromatography (GPC) of 1,000 to 500,000.

4. A process for producing vinylphenylpropionic acid derivatives represented by the following formula (1):

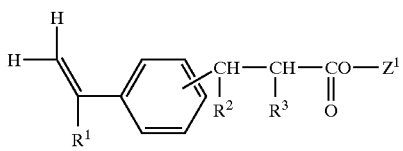 (1)

wherein $R^1$ is a hydrogen atom or a methyl group, $R^2$ and $R^3$ may be the same or different and each is a hydrogen atom, an alkyl group having 1 to 8 carbon atoms which may be substituted or a phenyl group which may be substituted, and $Z^1$ is a group represented by the following formula (2):

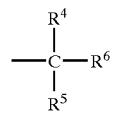 (2)

wherein $R^4$, $R^5$ and $R^6$ may be the same or different and each is a hydrogen atom, an alkyl group having 1 to 8 carbon atoms which may be substituted or a phenyl group which may be substituted, or any two of $R^4$, $R^5$ and $R^6$ may be bonded together with a carbon atom bonded thereto to form a cyclic aliphatic group, or a group represented by the following formula (3):

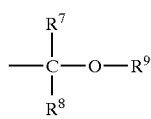 (3)

wherein $R^7$ and $R^8$ may be the same or different and each a hydrogen atom, an alkyl group having 1 to 8 carbon atoms which may be substituted or a phenyl group which may be substituted, $R^9$ is an alkyl group having 1 to 8 carbon atoms which may be substituted or a phenyl group which may be substituted, or any two of $R^7$, $R^8$ and $R^9$ may be bonded together with a carbon atom bonded thereto to form a cyclic aliphatic group, with proviso that the group represented by

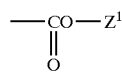

is an acid dissociable group which generates a carboxyl group (—COOH) in the presence of an acid, comprising the steps of:

(i) reacting an acetate represented by the following formula (4-1):

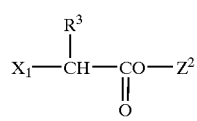 (4-1)

wherein $R^3$ is as defined in the above formula (1), $Z^2$ is a group represented by the following formula (2'):

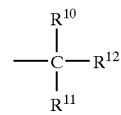 (2')

wherein $R^{10}$, $R^{11}$ and $R^{12}$ may be the same or different and each is a hydrogen atom, an alkyl group having 1 to 8 carbon atoms which may be substituted or a phenyl group which may be substituted, or any two of $R^{10}$, $R^{11}$ and $R^{12}$ may be bonded together with a carbon atom bonded thereto to form a cyclic aliphatic group, or a group represented by the above formula (3), and $X_1$ is an eliminating group, with a trialkylphosphine represented by the following formula (4-2):

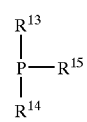 (4-2)

wherein $R^{13}$, $R^{14}$, and $R^{25}$ may be the same or different and each an alkyl group having 1 to 8 carbon atoms which may be substituted, to form a first quaternary phosphonium salt represented by the following formula (4-3):

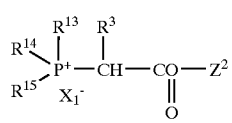 (4-3)

wherein $R^3$ is as defined in the above formula (1), $Z^2$ and $X_1$ are as defined in the above formula (4-1), and $R^{13}$, $R^{14}$ and $R^{15}$ are as defined in the above formula (4-2), (ii) reacting the formed first quaternary phosphonium salt with a base to form a phosphorus ylide represented by the following formula (4-4):

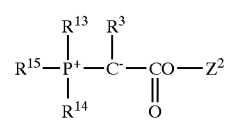 (4-4)

wherein $R^3$ is as defined in the above formula (1), $Z^2$ is as defined in the above formula (4-1), and $R^{13}$, $R^{14}$ and $R^{15}$ are as defined in the above formula (4-2), (iii) reacting the formed phosphorus ylide with a styrene derivative represented by the following formula (4-5):

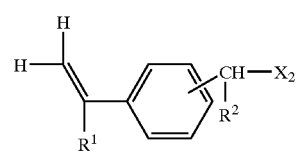 (4-5)

wherein $R^1$ and $R^2$ are as defined in the above formula (1), and $X_2$ is an eliminating group, to form a second quaternary phosphonium salt represented by the following formula (4-6):

(4-6)

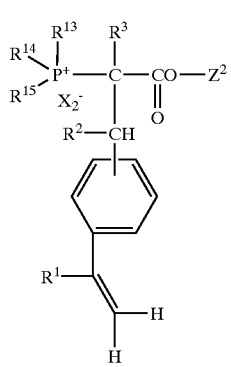

wherein $R^1$, $R^2$ and $R^3$ are as defined in the above formula (1), $Z^2$ is as defined in the above formula (4-1), and $R^{13}$, $R^{14}$ and $R^{15}$ are as defined in the above formula (4-2), and (iv) hydrolyzing the formed quaternary phosphonium salt.

5. A polymer which comprises a recurring unit represented by the following formula (1'):

(1')

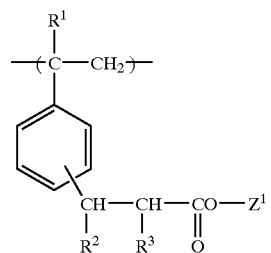

wherein $R^1$, $R^2$, $R^3$ and $Z^1$ are as defined in the above formula (1) of claim 4, and which has a weight average molecular weight in terms of polystyrene measured by gel permeation chromatography (GPC) of 1,000 to 500,000.

6. A radiation sensitive resin composition which comprises (A) the polymer of claim 5 and (B) a radiation sensitive acid generating agent.

7. A radiation sensitive resin composition which comprises (A) the polymer of claim 3 and (B) a radiation sensitive acid generating agent.

* * * * *